(12) United States Patent
Chen et al.

(10) Patent No.: US 9,873,862 B2
(45) Date of Patent: Jan. 23, 2018

(54) MAINTENANCE AND PROPAGATION OF MESENCHYMAL STEM CELLS

(71) Applicants: THE BOARD OF TRUSTEES OF THE UNIVERSITY OF ARKANSAS, Little Rock, AR (US); THE UNITED STATES OF AMERICA AS REPRESENTED BY THE DEPARTMENT OF VETERANS AFFAIRS, Washington, DC (US)

(72) Inventors: Xiao-Dong Chen, San Antonio, TX (US); Robert L. Jilka, Little Rock, AR (US)

(73) Assignees: The Board of Trustees of the University of Arkansas, Little Rock, AR (US); The United States of America as Represented by the Department of Veterans Affairs, Washington, DC (US)

( * ) Notice: Subject to any disclaimer, the term of this patent is extended or adjusted under 35 U.S.C. 154(b) by 331 days.

(21) Appl. No.: 14/596,777

(22) Filed: Jan. 14, 2015

(65) Prior Publication Data

US 2015/0210983 A1    Jul. 30, 2015

Related U.S. Application Data

(60) Continuation of application No. 13/762,887, filed on Feb. 8, 2013, now Pat. No. 8,961,955, which is a division of application No. 13/297,966, filed on Nov. 16, 2011, now Pat. No. 8,388,947, which is a division of application No. 11/625,763, filed on Jan. 22, 2007, now Pat. No. 8,084,023.

(51) Int. Cl.
| | |
|---|---|
| *C12N 5/0775* | (2010.01) |
| *A61K 35/28* | (2015.01) |
| *C12M 3/00* | (2006.01) |
| *C12M 1/12* | (2006.01) |
| *A61K 35/12* | (2015.01) |

(52) U.S. Cl.
CPC ............ *C12N 5/0662* (2013.01); *A61K 35/28* (2013.01); *C12M 21/08* (2013.01); *C12M 25/14* (2013.01); *C12N 5/0663* (2013.01); *C12N 5/0668* (2013.01); *A61K 2035/124* (2013.01); *C12N 2513/00* (2013.01); *C12N 2533/90* (2013.01)

(58) Field of Classification Search
CPC .................................................. C12N 5/0662
See application file for complete search history.

(56) References Cited

U.S. PATENT DOCUMENTS

| | | | |
|---|---|---|---|
| 5,843,780 A | 12/1998 | Thomson | 435/363 |
| 6,030,836 A | 2/2000 | Thiede et al. | 435/347 |
| 6,200,806 B1 | 3/2001 | Thomson | 435/366 |
| 6,284,284 B1 | 9/2001 | Naughton | 424/520 |
| 6,387,367 B1 | 5/2002 | Davis-Sproul et al. | 424/93.1 |
| 6,800,480 B1 | 10/2004 | Bodnar et al. | 435/325 |
| 6,911,201 B1 | 6/2005 | Merchav et al. | 424/93.7 |
| 8,084,023 B2 | 12/2011 | Chen et al. | 424/93.1 |
| 2003/0113812 A1 | 6/2003 | Hemperly | 435/7.2 |
| 2005/0013872 A1 | 1/2005 | Freyman | 424/549 |
| 2005/0265980 A1 | 12/2005 | Chen et al. | 424/93.7 |
| 2007/0128722 A1 | 6/2007 | Lin | 435/366 |
| 2008/0038352 A1 | 2/2008 | Simpson et al. | 424/484 |
| 2008/0175816 A1 | 7/2008 | Chen et al. | 424/484 |
| 2009/0081784 A1 | 3/2009 | Vodyanyk et al. | 435/372 |
| 2010/0093077 A1 | 4/2010 | McClelland et al. | 435/325 |

FOREIGN PATENT DOCUMENTS

WO    WO 2005/094898    2/2005

OTHER PUBLICATIONS

Sakai et al. (Biomaterials. 2003; 24: 3531-3541).*
Grayson et al. (Biotechnol. Prog. 2004; 20: 905-912).*
Datta et al. (Biomaterials. 2005; 26: 971-977).*
Baraniak et al (Regen Med. 2010; 5(1): 121-143).*
Abe et al., "Essential requirement of BMPs/2/4 for both osteoblast and osteoclast formation in murine bone marrow cultures from adult mice: antagonism by noggin," *J. of Bone and Mineral Research*, 15(4):663-673, 2000.
Baksh et al., "Adult mesenchymal stem cells: characterization, differentiation and application in cell and gene therapy," *Cell Mol. Med.*, 8(3):301-316, 2004.
Baraniak et al., "Stem cell paracrine actions and tissue regeneration," *Regen Med.*, 5(1):121-143, 2010.
Bi et al., "Extracellular matrix proteoglycans control the fate of bone marrow stromal cells," *J. Biol. Chem.*, 280(34):30481-30489, 2005.
Bianco et al., "Bone marrow stromal stem cells: nature, biology and potential applications," *Stem Cells*, 19:180-192, 2001.
Bianco et al., "Expression and localization of the two small proteoglycans biglycan and decorin in developing human skeletal and non-skeletal tissues," *J. Histrochemistry and Cytochemistry*, 38(11):1549-1563, 1990.
Chen et al., "The small leucine-rich proteoglycan biglycan modulates BMP-4-induced osteoblast differentiation," *FASEB J.*, 18:948-958, 2004.
Chow et al., "Modeling p02 distributions in the bone marrow hematopoietic compartment. I. Krogh's model," *Biophysical J.*, 81:675-684, 2001.
D'Ippolito et al., "Marrow-isolated adult mulilineage inducible (MIAMI) cells, a unique population of postnatal young and old human cells with extensive expansion and differentiation potential," *J. of Cell Science*, 117:2871-2981, 2004.

(Continued)

*Primary Examiner* — Scott Long
(74) *Attorney, Agent, or Firm* — Norton Rose Fulbright US LLP

(57) ABSTRACT

Various embodiments of the present invention include compositions, materials and methods for maintaining and propagating mammalian mesenchymal stem cells in an undifferentiated state in the absence of feeder cells and applications of the same.

4 Claims, 16 Drawing Sheets

(56) References Cited

OTHER PUBLICATIONS

Datta et al., "Effect of bone extracellular matrix synthesized in vitro on the osteoblastic differentiation of marrow stromal cells," *Biomaterials*, 26:971-977, 2005.

Dennis et al., "A quadripotential mesenchymal progenitor cell isolated from the marrow of an adult mouse," *J. Bone Miner Res*, 14(5):700-709, 1999.

Digregorio et al., Attenuation of the self-renewal of transit-amplifying osteoblast progenitors in the murine bone marrow by 17N-estradiol, *J. Clinical Investigation*, 107:803-812, 2001.

Dippolito et al., Low oxygen tension inhibits osteogenic differentiation and enhances stemness of human MIAMI cells, *Bone*, 30:513-522, 2006.

Engler et al., Matrix elasticity directs stem cell lineage specification, *Cell*, 126:677-689, 2006.

Freidman, "Molecular mechanisms of hepatic fibrosis and principles of therapy", *Journal of Gastroenterology*, 32:424-430, 1997.

Gospodarowicz et al., "Comparison of the ability of basement membranes produced by corneal endothelial and mouse-derived endodermal PF-HR-9 cells to support the proliferation and differentiation of bovine kidney tubule epithelial cells in vitro," *J. of Cell Biology*, 99:947-961, 1984.

Grayson et al., "Human Mesenchymal Stem Cells Tissue Development in 3D PET Matrices," *Biotechnol. Prog.*, 20:905-912, 2004.

International Search Report, issued in International Patent Application No. PCT/US2008/51598, dated Aug. 15, 2008.

Jiang et al., "Pluripotency of mesenchymal stem cells derived from adult marrow," *Nature*, 418: 41-49, 2002.

Katayama et al., "Signals from the sympathetic nervous system regulate hematopoietic stem cell egress from bone marrow," *Cell*, 124:407-421, 2006.

Klein, "The extracellular matrix of the hematopoietic microenvironment," *Experientia*, 51:914-926, 1995.

Krebsbach et al., "Bone formation in vivo: comparison of osteogenesis by transplanted mouse and human marrow stromal fibroblasts," *Transplantation*, 63(8):1059-1069, 1997.

Mizutani et al., "The nature of bone morphogenetic protein (BMP) fractions derived from bovine bone matrix gelatin," *Clin. Orthop. Relat. Res.*, 171:213-223, 1982.

Moriscot et al., "Human bone marrow mesenchymal stem cells can express insulin and key transcription factors of the endocrine pancreas developmental pathway upon genetic and/or microenvironmental manipulation in vitro," *Stem Cells*, 23:594-604, 2005.

Office Communication, issued in U.S. Appl. No. 11/625,763, dated Nov. 25, 2008.

Office Communication, issued in U.S. Appl. No. 11/625,763, dated Aug. 15, 2008.

Office Communication, issued in U.S. Appl. No. 11/625,763, dated May 3, 2011.

Office Communication, issued in U.S. Appl. No. 11/625,763, dated Mar. 5, 2010.

Office Communication, issued in U.S. Appl. No. 11/625,763, dated Mar. 20, 2009.

Office Communication, issued in U.S. Appl. No. 11/625,763, dated Jun. 29, 1010.

Office Communication, issued in U.S. Appl. No. 11/625,763, dated Nov. 3, 2009.

Peister et al., "Adult stem cells from bone marrow (MSCs) isolated from different strains of inbred mice vary in surface epitopes, rates of proliferation and differentiation potential," *Blood*, 103(5): 1662-1668, 2004.

Raines et al., "The extracellular matrix can regulate vascular cell migration, proliferation, and survival: relationships to vascular disease", *International Journal of Experimental Pathology*, 81:173-182, 2000.

Sakai et al., "Transplantation of mesenchymal stem cells embedded in Atelocollagen® gel to the intervertebral disc: a potential therapeutic model for disc degeneration," *Biomaterials*, 24:3531-3541, 2003.

Sekiya et al., "Expansion of human adult stem cells from bone marrow stroma: conditions that maximize the yields of early progenitors and evaluate their quality," *Stem Cells*, 20:530-541, 2002.

Sethe et al., "Aging of mesenchymal stem cells," *Ageing Research Reviews*, 5:91-116, 2005.

Tamama et al., "Epidermal Growth Factor as a Candidate for Ex Vivo Expansion of Bone Marrow—Derived Mesenchymal Stem Cells," *Stem Cells*, 24(3):686-695, 2006.

Tamama et al., "Epidermal growth factor as candidate for ex vivo expansion of bone marrow-derived mesenchymal stem cells," *Stem Cells Express*, pp. 1-40, 2005.

* cited by examiner

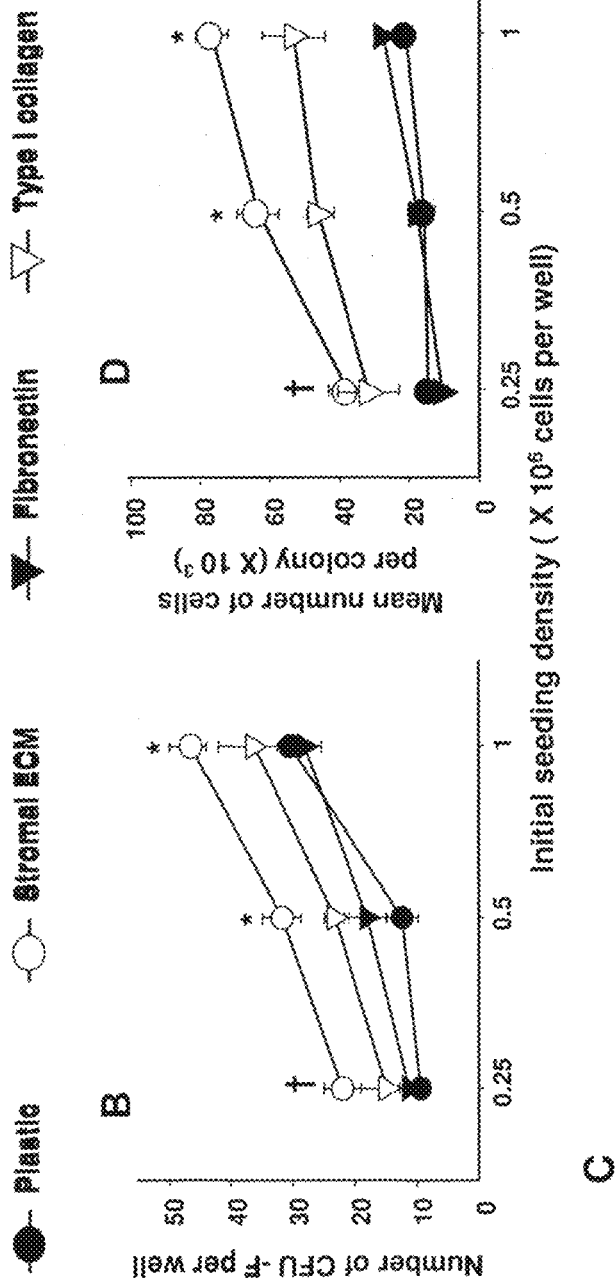
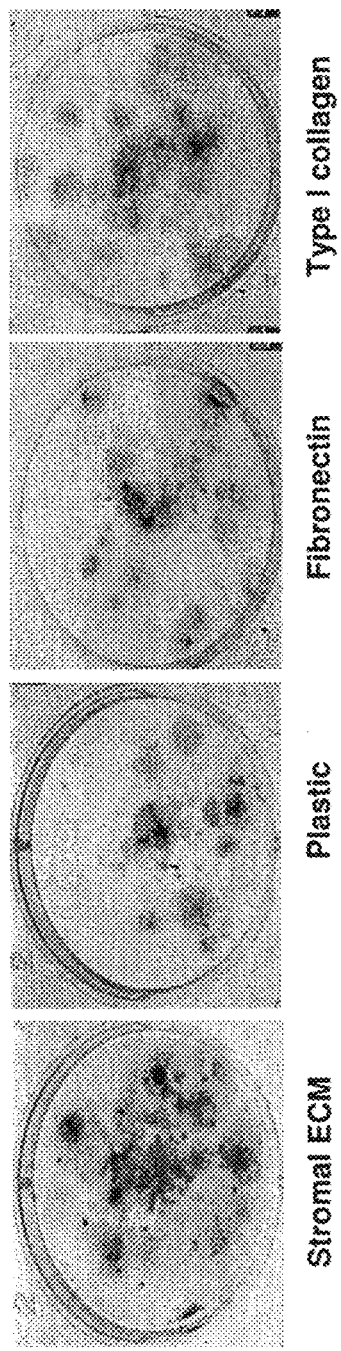
*Figs. 3B, 3C and 3D*

MAINTENANCE AND PROPAGATION OF MESENCHYMAL STEM CELLS

CROSS-REFERENCE TO RELATED APPLICATIONS

This application is a continuation of U.S. patent application Ser. No. 13/762,887, filed Feb. 8, 2013, which is a divisional of U.S. patent application Ser. No. 13/297,966 filed Nov. 16, 2011, now U.S. Pat. No. 8,388,947, which is a divisional of U.S. patent application Ser. No. 11/625,763 filed Jan. 22, 2007, now U.S. Pat. No. 8,084,023. The entire contents of each of the above-referenced disclosures are specifically incorporated herein by reference without disclaimer.

STATEMENT REGARDING FEDERALLY SPONSORED RESEARCH

This work was supported by the Department of Veterans Affairs, and grants R21 AG025466 and P01 AG13938 from the National Institutes of Health. The government may have certain rights in this invention.

BACKGROUND OF THE INVENTION

Mesenchymal stem cells (MSCs) are characterized by their ability to produce daughter stem cells and also to differentiate into marry distinct cell types including, but not limited to, osteoblasts, stromal cells that support hematopoiesis and osteoclastogenesis, chondrocytes, myocytes, adipocytes of the bone marrow, neuronal cells and β-pancreatic islet cells. Thus, MSCs are able to provide the appropriate number of osteoblasts and stromal cells needed for bone development, bone remodeling and hematopoiesis throughout life.

MSCs are extremely rare in the bone marrow and earlier attempts to expand them ex vivo from rodent or human marrow have proven difficult. Moreover, MSCs tend to lose their stem cell properties under traditional cell culture conditions. This situation has impaired the use of MSCs for practical purposes, such as, for example, therapeutic purposes.

The loss of MSC properties in vitro suggests that a critical feature of the marrow environment in vivo, which is responsible for the retention of stem cell properties, is missing its standard culture systems. The present invention illustrates that mesenchymal stem cells require a specialized microenvironment or niche that supports their self-renewal capability, and maintains their multipoteniality while facilitating differentiation in response to appropriate signals.

MSCs reside within the bone marrow, which consists of stromal cells, adipocytes, vascular elements, and sympathetic nerve cells arrayed within a complex extracellular matrix (ECM).[4,5]. The bone marrow ECM may comprise molecule selected from the group consisting of collagens I, III, IV, V and VI, fibronectin, and laminin. The bone marrow ECM may also comprise molecules selected from the group consisting of adhesive proteins, large molecular weight proteoglycans like syndecan and perlecan, and members of the small leucine-rich proteoglycan family including biglycan and decorin.[6,7]

The present inventors demonstrate that collars of marrow-derived MSCs on a cell-free ECM made by marrow-derived stromal cells promotes self-renewal of MSCs and helps maintain the MSCs in an undifferentiated state. Use present inventors further demonstrate that following expansion on this ECM, functional MSCs were increased as evidenced by increased formation of bone and hematopoietic marrow tissue following subcutaneous transplantation of in vitro expanded MSCs to immuno-compromised mice.

Stem cells may divide asymmetrically to give a daughter stem cell and a more differentiated progeny, or symmetrically to give two identical daughter stem cells or two more differentiated cells. Regulation of these events allows preservation of stem cells throughout life, and expansion of stem cells as well as production of differentiated progeny when needed for tissue repair.[1] Various embodiments of the present invention illustrate that culture of MSCs on an ECM made by marrow-derived stromal cells promotes symmetric division to produce identical daughter cells whereas plastic favors production of differentiated progeny by symmetric or asymmetric cell division. Moreover, the MSCs expanded on the marrow ECM retain the ability to form a complete bone like structure comprising a calcified matrix made by osteoblasts, hematopoietic marrow containing adipocytes, and stromal sells that support hematopoietic and osteoclastogenesis. In contrast, growth of MSCs on tissue culture plastic results is eventual loss of self-renewal capacity and multipotentiality, and this is associated with expression of the osteoblast phenotype. Although cells expanded on plastic did form bone in vivo as previously reported,[8] they made less bone and minimal hematopoietic marrow.

Culture of MSCs in the presence of three-dimensional (3D) stromal cell derived ECM allows for attachment, self-renewal, and retention of multipotentiality of MSCs, whereas culture of MSCs under two-dimensional (2D) conditions with or without certain ECM proteins like type I collagen or fibronectin does not.

Loss of stem cell properties, coincident with so-called "spontaneous" differentiation when MSCs are cultured on plastic, may actually represent the response of MSCs to growth factors produced endogenously in these cultures. Indeed, autocrine/paracrine production of BMP2/4 mediates the production of osteoblastic cells when MSCs are cultured on plastic.[9] BMPs bind strongly to collagen as well as small proteoglycans such as biglycan.[10] Embodiments of the present invention demonstrate that the BCM sequestered the BMP2 produced by cultured marrow cells, and this at least partially explains why MSCs retained an undifferentiated phenotype when cultured on a collagenous ECM. Other pro-differentiating proteins may also be sequestered by the ECM.

MSCs lose their multipotentiality when cultured on tissue culture plastic. Previous attempts to overcome this limitation have utilized culture on fibronectin matrices under low oxygen tension (5%)[11,12] to mimic the microenvironment of the bone marrow,[13] or culture at low seeding density in low serum in the presence of growth factors.[14-16] These conditions permitted expansion of murine and human MSCs for as many as 60 population doublings, but the full differentiation potential and cellular composition of these preparations remains unclear.

The present invention illustrates that the marrow ECM forms past of the niche that supports MSCs in the bone marrow, and that the ECM regulates the balance between replication and differentiation in response to appropriate signals. Consequently, the 3D extracellular matrix culture system described herein provides a system for the expansion of functional MSCs for practical applications. This system is invaluable for identification of the contribution of specific ECM components in regulating the behavior of MSCs. Finally, the system is also useful for identifying the effect of aging and/or hormonal changes on the ability of the marrow ECM to maintain MSC function, and thereby contribute to the development of pathologies such as osteoporosis.

BRIEF SUMMARY OF THE INVENTION

The present inventors disclose mesenchymal stem cells (MSCs) cultured on an ECM made by marrow stromal cells thereby reconstituting the MSC niche. This ECM specifically promotes self-renewal of MSCs and retention of their multipotentiality. The present inventors demonstrate that the marrow ECM is useful for the maintenance of stemness, and that the ECM provides a vehicle for MSC expansion.

Cell-free three-dimensional (3D) matrices were prepared from cultured marine marrow stromal cells. The self-renewal and multipotentiality of murine MSCs maintained on this stromal cell-derived ECM were examined in vitro, and in vivo and compared to MSCs maintained on plastic, fibronectin, Type I collagen, or skin fibroblast-derived ECM.

Stromal cell-derived ECM may comprise collagen types I, III, and V, syndecan-1, perlecan, fibronectin, laminin, biglycan and decorin, and resembles the marrow ECM. This ECM preparation promotes self-renewal of MSCs, restrains their "spontaneous" differentiation toward the osteoblast lineage, and preserves their ability to differentiate into osteoblasts or adipocytes in response to BMP2 or rosiglitazone, respectively. In contrast, two-dimensional (2D) matrices made of Type I collagen or fibronectin, or skin fibroblast-derived 3D ECM, failed to do so. Moreover, transplantation of MSCs expanded on the stromal cell-derived ECM into immunocompromised mice generated five times more bone and eight times more hematopoietic marrow, as compared to MSCs expanded on plastic.

Thus, the ECM made by bone marrow stromal cells is useful for the maintenance of MSCs and provides a vehicle for the expansion of these cells ex vivo.

In one embodiment of the present invention, the inventors disclose a cellular composition comprising mammalian mesenchymal stem cells maintained in culture in an undifferentiated state. The cellular composition of mammalian mesenchymal stem cells comprises mammalian mesenchymal stem cells growing on an extracellular matrix.

In another embodiment of use present invention, the inventors disclose a composition for maintaining mammalian mesenchymal stem cells in culture in an undifferentiated state comprising an extracellular matrix.

The present inventors also disclose a method of maintaining mammalian mesenchymal stem cells in culture in an undifferentiated state comprising culturing mammalian mesenchymal stem cells in the presence of an extracellular matrix.

In a further embodiment of the present invention, the inventors disclose a cell culture apparatus for maintaining mammalian mesenchymal stem cells in an undifferentiated state comprising a substrate and an extracellular matrix.

Another method disclosed by the present inventors is a method of maintaining mammalian mesenchymal stem cells in an undifferentiated state comprising culturing mammalian mesenchymal stem cells in the presence of as inhibitor of BMP2 activity.

A further embodiment of the present invention is a bone forming composition comprising: (i) a cellular composition comprising mammalian mesenchymal stem cells grown on an extracellular matrix, and (ii) a transplantation vehicle.

The present inventors also disclose a method of generating bone in a patient in need thereof comprising: (i) obtaining mammalian mesenchymal stem cells; (ii) producing a bone forming composition by culturing said mammalian mesenchymal stem cells in vitro on an extracellular matrix and isolating differentiated mammalian mesenchymal stem cells from said culture; and (iii) administration of said bone forming composition to said patient.

BRIEF DESCRIPTION OF THE DRAWINGS

FIG. 3B illustrates CFU-F number as determined at indicated seeding densities.

FIG. 3C illustrates the appearance of CFU-F derived from cells cultured into a cell-free stromal cell-derived ECM, plastic, or 2D fibronectin or Type I collagen matrices.

FIG. 3D illustrates the number of cells per CFU-F colony as determined at indicated seeding densities. * $P<0.05$, n=3 vs. plastic or the 2D matrices containing fibronectin or Type I collages at the same density, † $P<0.05$, n=3 compared to plastic or the 2D matrices containing fibronectin.

FIG. 11A shows the measurements of bone area from 3 individual sections for each sample (S1 or S2).

DETAILED DESCRIPTION

Figure 1:
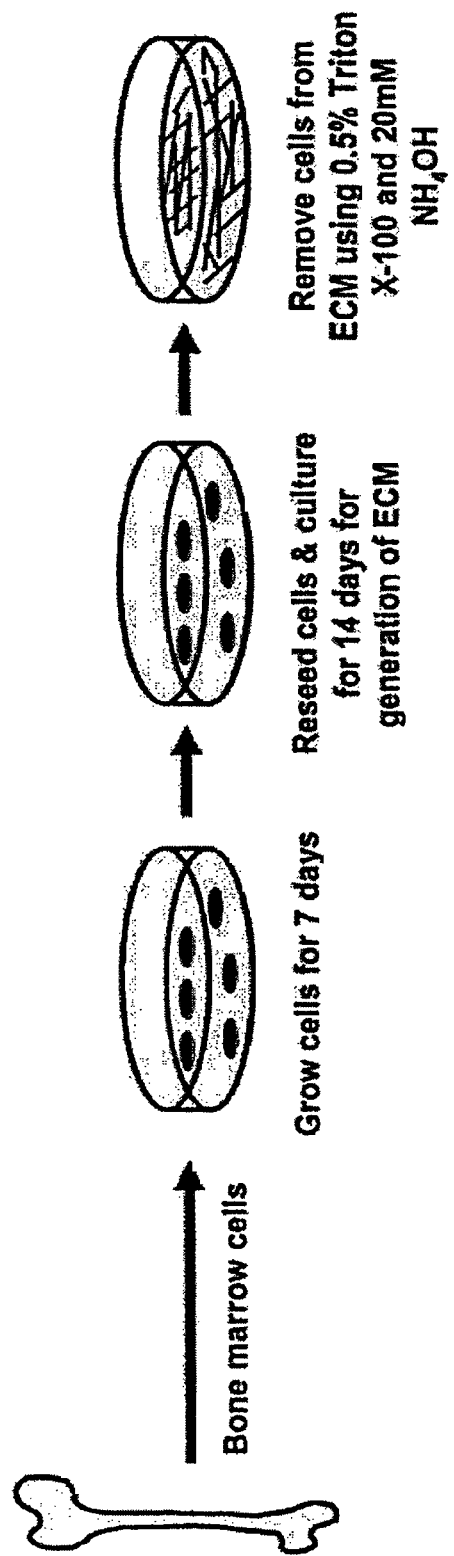
FIG. 1 illustrates various embodiment of the present invention including a method of manufacturing a composition for maintaining mammalian mesenchymal stem cells in culture in an undifferentiated state, and an exemplary cell culture apparatus for maintaining mammalian mesenchymal stem cells in culture in an undifferentiated state.

In various embodiments, the present invention provides a cellular composition of mammalian mesenchymal stem cells maintained in culture in an undifferentiated state. The cellular composition of mammalian mesenchymal stem cells may comprise mammalian mesenchymal stem cells growing on an extracellular matrix. The cellular composition may be essentially free of feeder cells. Additionally, the mammalian mesenchymal stem cells may proliferate on the extracellular matrix.

Mammalian mesenchymal stem cells may be obtained from various sources, including, but not limited to, bone marrow or other mesenchymal stem cell sources. Bone marrow cells may be obtained from various sources, such as, for example, iliac crest, femora, tibiae, spine, rib, or other medullary spaces. Other mesenchymal stem cell sources include, but are not limited to, embryonic yolk sac, placenta, umbilical cord, fetal and adolescent skin and blood. Isolating and establishing cultures of mesenchymal stem cells are generally-known to those of skill in the relevant art.

In some embodiments of the present invention, the mammalian mesenchymal stem cells forming the cellular composition may be selected from the group consisting of human mesenchymal stem cells and murine mesenchymal stem cells.

When maintained or propagated in culture, mammalian mesenchymal stem cells may divide symmetrically or asymmetrically. In some configurations of the present invention, the mammalian mesenchymal stem cells are capable of either symmetrical division or asymmetrical division. In particular embodiments, the present invention provides materials and methods which allow for the mammalian mesenchymal stem cells to divide symmetrically.

In various embodiments of the present invention, a cellular composition comprises mammalian mesenchymal stem cells and an extracellular matrix. In particular embodiments of the invention, the extracellular matrix comprises a marrow stromal cell derived extracellular matrix. For purposes of further illustration of the present invention, the marrow stromal cell derived extracellular matrix may be manufactured by obtaining marrow stromal cells, culturing said marrow stromal cells, lysing the marrow stromal cells and removing the lysed marrow stromal cells by washing. The composition that remains after washing is an extracellular matrix that is essentially free of marrow stromal cells and essentially free of feeder cells. Marrow stromal cells may be obtained and cultured by common methods that are apparent to one of skill in the relevant art.

The present invention provides for a composition for maintaining mammalian mesenchymal stem cells in culture in an undifferentiated state. Said composition comprises an extracellular matrix and said composition is essentially free of feeder cells. Mammalian mesenchymal stem cells of the present embodiment may be selected from the group consisting of human mesenchymal stem cells and murine mesenchymal stem cells. Furthermore, the composition comprising an extracellular matrix may be a marrow stromal cell derived extracellular matrix, in addition to being a marrow stromal cell derived extracellular matrix, the extracellular matrix may also be a three-dimensional matrix.

In various embodiments of the present invention, an extracellular matrix is disclosed and that extracellular matrix is a marrow stromal cell derived extracellular matrix. In particular embodiments, the extracellular matrix may compose type I collagen, type III collagen, type V collagen, syndecan-1, fibronectin, decorin, biglycan, perlecan, and laminin. As described herein, such an extracellular matrix may be manufactured by obtaining marrow stromal cells, entering said marrow stromal cells, lysing the marrow stromal cells and removing the lysed marrow stromal cells by washing. The composition that remains after washing is an extracellular matrix according to various embodiments of the present invention.

A further embodiment of the present invention provides a method of maintaining mammalian mesenchymal stem cells in culture is an undifferentiated state comprising culturing mammalian mesenchymal stem cells in the presence of an extracellular matrix. The culture of mammalian mesenchymal stem cells is essentially free of feeder cells. As previously stated, said mammalian mesenchymal stem cells may be selected from the group consisting of human mesenchymal stem cells and murine mesenchymal stem cells. Furthermore, said extracellular matrix may be a marrow stromal cell derived extracellular matrix, and said extracellular matrix may be a three-dimensional matrix. In various embodiments of the present method, said extracellular matrix may comprise type I collagen, type III collagen, type V collagen, syndecan-1, fibronectin, decorin, biglycan, perlecan, and laminin. The method provides for manufacture of the extracellular matrix by obtaining marrow stromal cells, culturing marrow stromal cells, lysing the marrow stromal cells and removing the lysed marrow stromal cells by washing.

Certain embodiments of the present invention provide a cell culture apparatus for maintaining mammalian mesenchymal stem cells in an undifferentiated state comprising a substrate and an extracellular matrix. The substrate of the cell culture apparatus may comprise a cell culture container or a substrate that may be placed within a cell culture container. A cell culture container may be selected from the group consisting of a flask, a Petri dish, a vat and a reactor. Other cell culture containers may be useful in the present embodiment.

The cell culture apparatus described above comprises an extracellular matrix, and said extracellular matrix may comprise a marrow stromal cell derived extracellular matrix. Furthermore, said extracellular matrix may be a three-dimensional matrix. Such an extracellular matrix may comprise type I collagen, type III collagen, type V collagen, syndecan-1, fibronectin, decorin, biglycan, perlecan, and laminin. Additionally, the extracellular matrix of the cell culture separates may be manufactured by obtaining marrow stromal cells, culturing marrow stromal cells on a substrate, lysing the marrow stromal cells and removing the lysed marrow stromal cells by washing. The substrate and extracellular matrix that remains associated with the substrate subsequent to washing may be useful as a cell culture apparatus. Said cell culture apparatus may be irradiated or treated with chemical agents and stored for periods of time, such as, for example, approximately one week, approximately one month, approximately two months, approximately three months or even approximately four months or more. Chemical agents that may be useful during such periods of storage include antibiotics and antifungal agents.

Also disclosed is a method of maintaining mammalian mesenchymal stem cells in undifferentiated state comprising culturing mammalian mesenchymal stem cells in the presence of an inhibitor of bone morphogenetic protein 2 (BMP2) activity. BMP2 is an osteogenic protein that belongs to the TGF-β superfamily of proteins and induces osteoblast differentiation. An exemplary inhibitor of BMP2 activity is an extracellular matrix that sequesters BMP2. Such an extracellular matrix may comprise a marrow stromal cell derived extracellular matrix, and such a matrix may be a three-dimensional matrix. Additionally, an extracellular matrix with BMP2 inhibiting activity may comprise type I collagen, type-III collagen, type V collagen, syndecan-1, fibronectin, decorin, biglycan, perlecan, and laminin. For purposes of the present embodiment the mammalian mesenchymal stem, cells may be selected from the group consisting of human mesenchymal stem cells and murine mesenchymal stem cells.

Another embodiment of the present invention provides a bone forming composition comprising: (i) a cellular composition comprising mammalian mesenchymal stem cells grown on as extracellular matrix, and (ii) a transplantation vehicle. The cellular composition of the present embodiment is essentially free of feeder cells. Additionally, the mammalian mesenchymal stem cells may be either human mesenchymal stem cells or murine mesenchymal stem cells. The extracellular matrix of the cellular composition may comprise a marrow stromal cell derived extracellular matrix. Additionally, the extracellular matrix of the cellular composition may be a three-dimensional matrix. By way of example, the extracellular matrix of the cellular composition may comprise type I collagen, type III collagen, type V collagen, syndecan-1, fibronectin, decorin, biglycan, perlecan, and laminin.

In order to manufacture the bone forming composition of the present embodiment, said extracellular matrix may be manufactured by obtaining marrow stromal cells, culturing marrow stromal cells on a substrate, lysing the marrow stromal cells and removing the lysed marrow stromal cells by washing. The mammalian mesenchymal stem cells may then be cultured on the substrate. The mammalian mesenchymal stem cells may then be removed from the substrate by techniques known to those of skill in the art or as described herein. The mammalian mesenchymal stem cells may then be combined with a transplantation vehicle, such as, for example, a transplantation vehicle comprising hydroxyapatite or an acceptable salt thereof. The transplantation vehicle may further comprise tricalcium phosphate. In various embodiments of the present invention, the transplantation vehicle may comprise a ceramic powder.

Such a bone forming composition as previously described may be administered to a mammal in need of bone formation. Such a mammal may include any mammal that has a bone condition requiring bone formation. Exemplary conditions that may require bone formation include, but are not limited to, such bone conditions as fracture, delayed unions, non-unions, distraction osteogenesis, osteotomy, osseointegration, and osteoarthritis. Mammals that may be benefited by the present embodiment include mammals, such as, for example, humans and mice.

A further embodiment of the present invention provides a method of generating bone in a patient in need thereof comprising: (i) obtaining mammalian mesenchymal stem cells; (ii) producing a bone forming composition by culturing said mammalian mesenchymal stem cells in vitro on an extracellular matrix and isolating undifferentiated mammalian mesenchymal stem cells from said culture; and (iii) administration of said bone forming composition to said patient. The mammalian mesenchymal stem cells of the present embodiment may be selected from the group consisting of human mesenchymal stem cells and murine mesenchymal stem cells. Additionally, the extracellular matrix of the present embodiment may comprise a marrow stromal cell derived extracellular matrix as previously described. In some configurations, the mammalian mesenchymal stem cells of the present embodiment may be allogeneic or autologous to said patient. Moreover, the patient may be a human patient, and in particular embodiments, the patient may be an aging human patient. An aging patient may be, for example, any patient who is at least 35 years old, at least 40 years older, at least 50 years old, or at least 60 years old, or older. In various aspects of the present embodiment, the bone forming composition may further comprise a transplantation vehicle, such as, for example, a ceramic powder. Such ceramic powders that are useful in the present invention include hydroxyapatite ceramic powders. Furthermore, the transplantation vehicle may comprise tricalcium phosphate.

The bone forming composition may be administered to a patient in need thereof concurrently with surgery for a bone condition, laparoscopically, by injection or by any other means known to one of skill in the relevant art. The bone forming composition may be administered locally or systemically.

In this manner, mesenchymal stem cells may be expanded and propagated in vitro and subsequently administered to a patient thereby providing the patient with a sufficient quantity and quality of mesenchymal stem cells such that the patient may be effectively treated for a condition requiring bone formation, bone remodeling, bone development or any other condition that is improved by the action of mesenchymal stem cells.

EXAMPLES

The following examples are further illustrative of the present invention, but it is understood that the invention is not limited thereto.

Animals.

Swiss Webster female mice, 6-8 weeks old, were obtained from Marian (Indianapolis, Ind.). The University of Arkansas for Medical Sciences Division of Laboratory Animal Medicine approved the animal use protocol.

Scanning Electron Microscopy.

Samples were washed three times with PBS and feed with 2% glutaraldehyde in 0.1M sodium cacodylate buffer (pH 7.2) for one hour and then transferred to 0.1 M cacodylate buffer solution. The specimens were dehydrated in ascending concentrations of ethanol (from 70% to 100%), embedded in peon resin (Poly/bed 812 Polysciences Int., Warrington, Pa.), and then coated with gold and palladium. After dehydration the coverslips were attached to a stub and sputtered with gold-palladium. The gold-palladium-coated cultures were examined using an FEI/Philips XL30 Field emission environmental scanning electron microscope (Hillsboro, Oreg.).

Immunohistochemistry.

Stromal cell-derived ECM, before or after removal of cells, was fixed for 30 minutes with 4% formaldehyde in PBS at room temperature, washed with PBS, and blocked with 5% normal goat serum containing 0.1% BSA in PBS for one hour. The matrices were then incubated with the relevant primary antibodies (1:10 dilution) in 2% goat serum for two hours. Antibodies against biglycan, collagen type I, III, V, fibronectin, decorin, perlecan, syndecan-1, and laminin, were purchased from Santa Cruz Biotechnology (Santa Cruz, Calif.). Non-specific isotype IgG (1:10 dilution) was used as a negative control. After washing with PBS, samples were incubated with the appropriate horseradish peroxidase-conjugated secondary antibody (1:100 dilution) for one hour, developed with a 3,3'-diaminobenzidine substrate-chromogen system (Dako Corp., Carpinteria, Calif.) for five minutes, and then counterstained with methyl green.

Determination of Colony-Forming Unit Fibroblast (CFU-F), Osteoblast (CFU-OB), and Adipocyte (CFU-AD).

Freshly isolated murine femoral marrow cells were plated into 6-well plates at the indicated seeding densities, incubated for four hours at 37° C. to allow attachment of adherent cells, and washed twice with PBS to remove the non-adherent cells. Then, irradiated guinea pig feeder cells ($3\times10^6$) were added immediately in 4 ml of the α-MEM medium described above containing 1 mM L-ascorbate-2-phosphate (Wako Chemicals, Richmond, Va.). After approximately 10 to 12 days (CFU-F) or 25 days (CFU-OB), colonies were visualized with crystal violet or Von Kossa staining, respectively. For determination of CPU-AD, 100 nM rosiglitazone or vehicle (dimethylsulfoxide) was added to the cell cultures at day seven. On day 25, the cultures were stained with Von Kossa to visualize colonies containing mineralizing osteoblasts and with Oil Red O to visualize adipocytes. Colonies containing more than 50 cells were counted using a dissecting microscope.

Measurement of MSG self-renewal has been previously described.[17] Briefly, freshly isolated bone marrow cells were pre-cultured onto 6-well plates with or without the cell-free ECM or pre-cultured in a type I collagen, gel at $7\times10^6$ cells per well for 7 days. Cells were collected following treatment with collagenase and reseeded onto standard tissue culture plastic with irradiated guinea pig feeder cells in 4 ml of the α-MEM medium described above containing 1 mM L-ascorbate-2-phosphate for CFU-F CFU-OB, and CFU-AD assays.

Quantification of Gene Expression in Cultured Bone Marrow Cells.

Total RNA was extracted using Ultraspec reagent (Biotecx Laboratories, Inc., Houston, Tex.). RNA (2 µg) was reverse-transcribed using a High Capacity cDNA Archive Kit (Applied Biosystems Foster City, Calif.). The transcripts of interest, and that of the housekeeping gene GAPDH, were amplified from cDNA by real-time PCR using TaqMan Universal PCR Master Mix and Assay Demand or Assay by Design primer and probe sets (Applied Biosystems). Amplification and detection were carried out with an ABI Prism 7300 Sequence Detection System (Applied Biosystems) as follows: denaturation at 95° C. for 10 minutes, 40 cycles of amplification including denaturation at 94° C. for 15 seconds and annealing/extension at 60° C. for one minute. Gene expression was quantified by subtracting the GAPDH threshold cycle (Ct) value from the Ct value of the gene of interest, and expressed as $2^{-\Delta Ct}$, as described by the protocol of the manufacturer.

Measurement of Alkaline Phosphatase (ALP) Activity and Osteocalcin Secretion in Response to BMP2.

Freshly isolated murine bone marrow cells were cultured in α-MEM described above for 15 days. For measurement of ALP response, FBS was reduced to 2% and then human recombinant BMP2 (R&D Systems, Inc., Minneapolis, Minn.) was added. After 48 hours, cells were lysed (20 mM Tris, 0.5 mM $MgCl_2$, 0.1 mM $ZnCl_2$ and 0.1% Triton X) and ALP activity was determined using an alkaline phosphatase kit (Sigma Chemical Co., St. Louis, Mo.). The ALP value was normalized by the amount of protein in the lysates, and was expressed as ALP activity/minute/µg. For measurement of the osteocalcin response, medium was removed six days after addition of BMP2, and the osteocalcin levels were measured by RIA (Biomedical Technologies Inc., Stoughton, Mass.).

Measurement of BMP2.

Murine bone marrow cell cultures were established on plastic or on the marrow stromal cell-derived ECM 6-well plates. After 15 days, the supernatant was collected. After extensive rinsing, BMP2 was extracted from the ECM/cell layer using 2M urea, 2% SDS, 10% glycerol and 10 mM Tris-HCl pH 6.8.[18] The amount of BMP2 in the culture supernatant and the extracts was measured using a murine specific ELISA Assay Kit (R&D Systems, Minneapolis, Minn.).

In Vivo Bone Formation.

Marrow cells were cultured for seven days on plastic or the stromal cell-derived ECM. Adherent cells ($1\times10^6$) were loaded into a transplantation vehicle such as, for example, hydroxyapatite/tricalcium phosphate (HA/TCP) ceramic powder (Zimmer Inc, Warsaw, Ind., USA), and transplanted subcutaneously into the dorsal surface of 10-week-old immunodeficient beige mice (NIH-bg-nu-xid, Harlan Sprague Dawley, Indianapolis, Ind.), as previously described.[8,19] Three transplants were made for each pre-culture system. Transplants were harvested after four or eight weeks, fixed in 10% phosphate buffered formalin at 4° C. for 24 hrs, decalcified with 5% EDTA (pH8.0) at room temperature for 1-2 weeks, and then embedded in paraffin. Each ossicle was bisected, and three sections (10 μm) were cut from each part at 100 μm intervals. A total of nine H&E stained sections were used for clarification. The percentage of the area of new bone and hematopoietic marrow formed in transplants was measured by using Osteometrics image analysis software (Ostomeasure version 3.00, Osteometrics Inc., Atlanta, Ga.).

Statistical Analysis.

All data are presented as mean±standard deviation. Statistical analyses were done by using Student's t test or one-way ANOVA. Differences of $P<0.05$ were considered significant.

Example 1

FIG. 1 illustrates an exemplary method for manufacturing a cell culture apparatus for maintaining or propagating MSCs in culture in an undifferentiated state.

Freshly isolated murine femoral marrow cells were seeded onto tissue culture plastic at $3\times10^5$ cells/cm$^2$, and cultured for seven days in α-MEM (Life Technologies, Grand Island, N.Y.), supplemented with glutamine (2 mM), penicillin (100 U/ml), streptomycin (100 μg/ml) (Sigma Chemical Company, St. Louis, Mo.), and 15% pre-selected fetal bovine serum (FBS, Atlanta Biologicals, Lawrenceville, Ga.). For preparation of skin fibroblasts, the ventral skin from 2-5 day old mice were removed, rinsed in PBS, and cut into 1-mm$^2$ pieces. The tissue was incubated with 400 U/ml collagenase for 40 minutes at 37° C., rinsed with PBS, and cultured in high glucose DMEM medium containing 10% FBS, glutamine (2 mM) and penicillin (100 U/ml) until primary fibroblasts migrated out of the samples onto the culture plates reaching 70% confluence. Fibroblasts were collected, and frozen for storage or used between passages two and six for the establishment of ECM.

To prepare ECM, cells were seeded onto Thermanox plastic cover slips coated with fibronectin at $1\times10^4$ cells/cm$^3$, and cultured for seven days in the α-MEM medium described above. Then ascorbic acid (50 μg/ml) (Sigma Chemical Company, St. Louis, Mo.) was added to the cell cultures for an additional eight days. After extensive washing with PBS, cells were removed from the BCM by incubation with 0.5% Triton X-100 containing 20 mM NH$_4$OH in PBS for five minutes at 37° C. The ECM was then treated with DNase at 100 u/ml (Sigma Chemical Company, St. Louis, Mo.) for one hour at 37° C. The plates were washed with PBS three times, then 2.0 ml of PBS containing 50 μg/ml gentamicin and 0.25 μg/ml fungizone was added to the plates, and the plates were stored at 4° C. up to four months.

Example 2

Preparation of a Marrow Stromal Cell-Derived ECM.

Figure 2A:
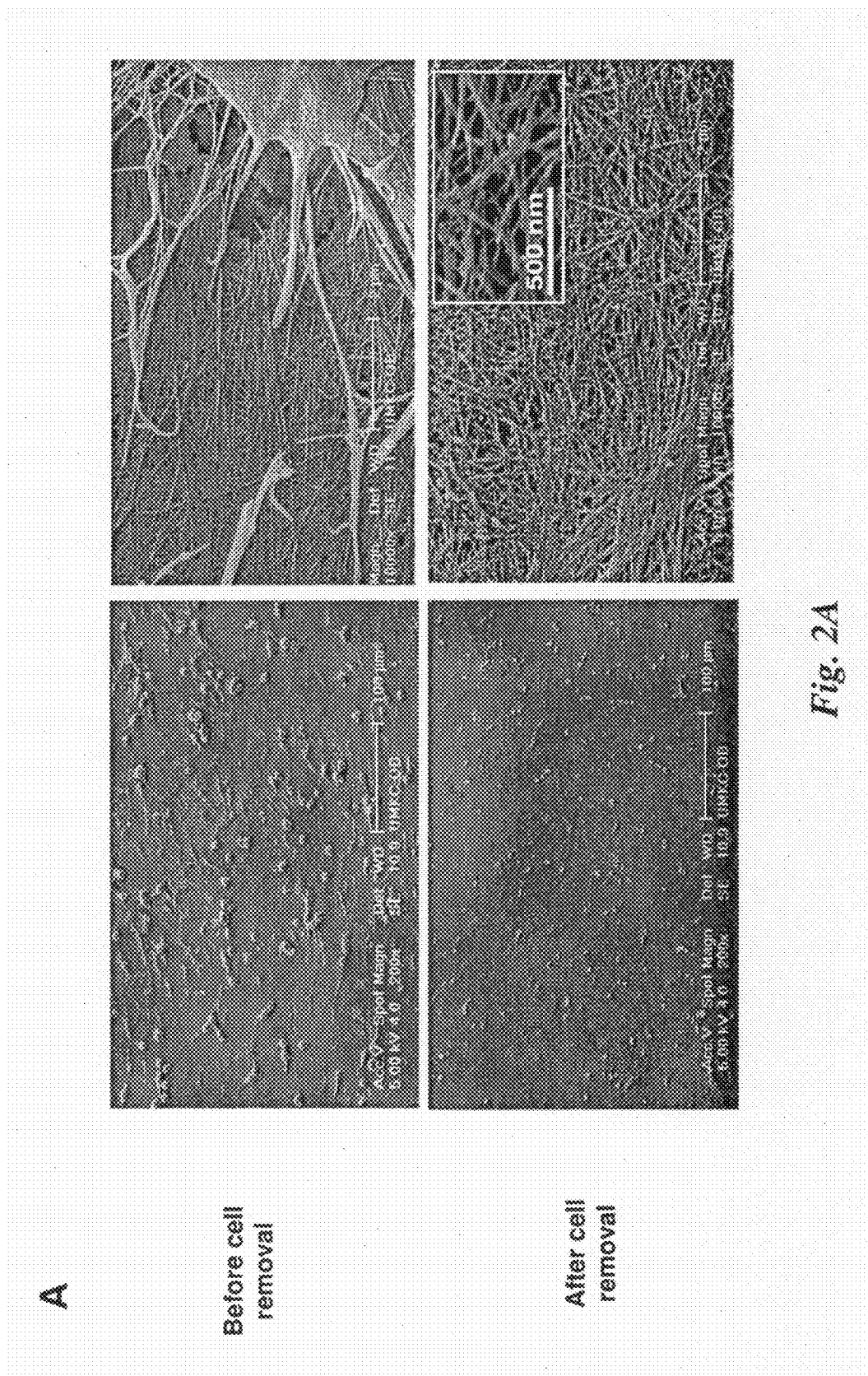
FIG. 2A illustrates SEM images of stromal cell-derived ECM before and after removing cells. The left panels show the ECM made by cultured marrow stromal cells before and after marrow stromal cell removal at low magnification. The right panels, at high magnification, show that the structure of the ECM is very similar before and after cell removal. Inset: enlargement of high magnification image after cell removal.

Scanning electron microscopy (SEM) revealed that stromal cells cultured from murine femoral bone marrow elaborated a fibrillar ECM (FIG. 2A). Prior to studying the behavior of MSCs on this ECM, the stromal cells were lysed with 0.5% Triton X-100 containing 20 nM NH$_4$OH followed by DNase treatment to digest remaining nuclear contaminants.[20] The resulting 3D matrix contained fibers of approximately 25 nm diameter and was approximately 100 μm thick as determined by transmission electron microscopy (data not shown).

Figure 2B:
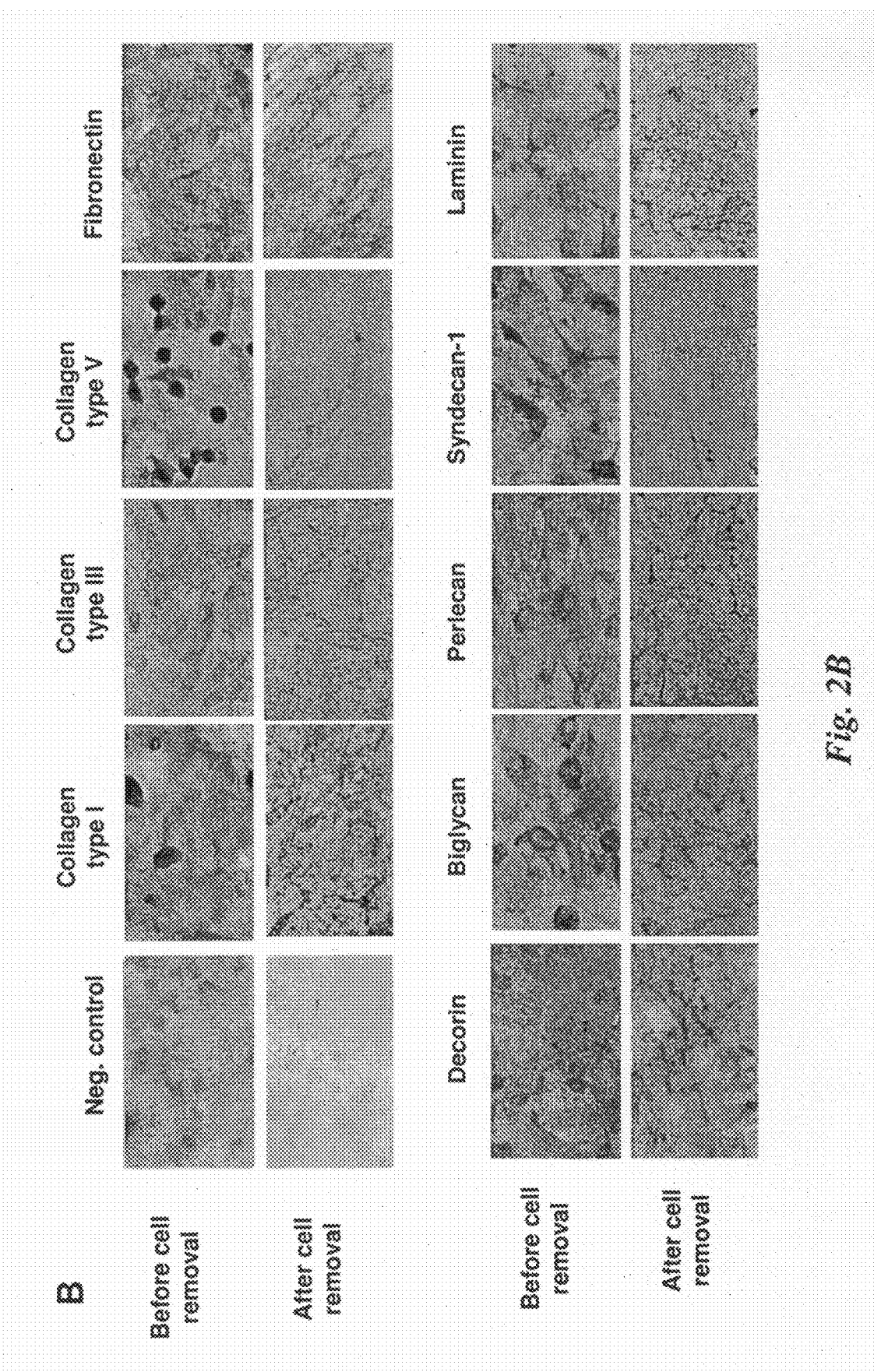
FIG. 2B illustrates immunohistochemical staining before and after marrow stromal cell removal for components of cell-free ECM made by cultured marrow stromal cells. Original magnification: 200×.

When examined prior to removal of stromal cells, immunostaining revealed high levels of collagen types I, III, V, syndecan-1, perlecan, fibronectin, laminin, biglycan and decorin associated with both stromal cells and the ECM (FIG. 2B). The protein composition of the ECM was only modestly affected by the cell extraction procedure as indicated by retention of immunostaining for all of the proteins that were examined except for collagen type V (FIG. 2B).

Example 3

Culture on Stromal Cell-Derived ECM Facilitates Retention of MSC Properties.

Figure 3A:
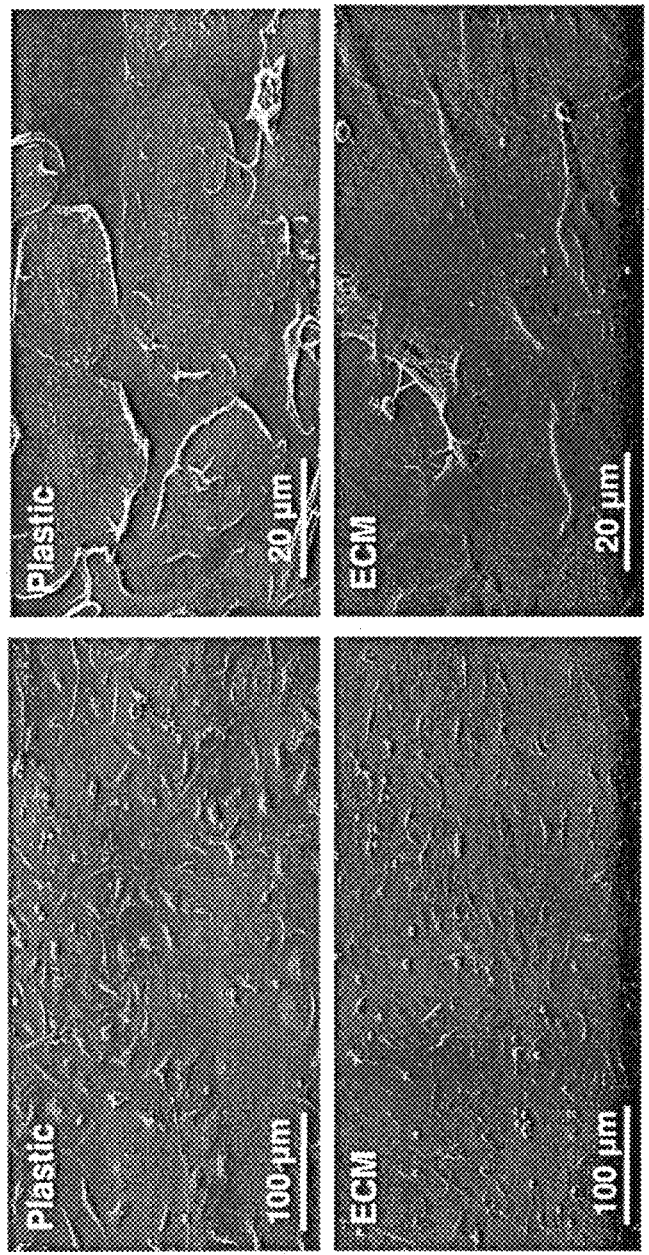
FIG. 3A illustrates SEM images of bone marrow cells cultured on tissue culture plastic (top panels) or stromal cell-derived ECM (lower panels) obtained after 5 days of culture.

The ECM affects MSC adherence and proliferation. MSCs were detected and quantified by their ability to form a colony of fibroblastic cells.[21] These colony-forming cells, called colony forming unit-fibroblasts (CFU-F), comprise MSCs. After five days of culture, most of the cells in the colony were embedded inside of the collagenous matrix and exhibited a fibroblastic morphology with extensive cellular processes. In contrast, cells cultured on tissue culture plastic were round and flat (FIG. 3A).

When cultured on the stromal cell-derived ECM, there was approximately a two to three fold increase in the number of CFU-F as compared to tissue culture plastic, demonstrating that the ECM promoted MSC attachment (FIGS. 3B and 3C). 2D ECM preparations, made by coating tissue culture plasticware with fibronectin or Type I collagen, were less effective (FIGS. 3B and 3C). Moreover, the colonies that developed on the stromal cell-derived ECM contained approximately four-fold more cells than colonies that developed on plastic or fibronectin, whereas colonies formed on Type I collagen matrix contained only approximately two-fold more cells than the colonies that developed on plastic or fibronectin (FIG. 3D). These findings indicate that a collagen-containing ECM uniquely promotes the proliferative capacity of MSCs and/or their transit amplifying progeny.

Cells in parallel cultures were detached by treating with 400 U/ml collagenase and the total number of cells per well was counted using a hemocytometer. The mean number of cells per colony was estimated by dividing the number of cells per well by number of colonies per well.

Example 4

Figures 4A, 4B:
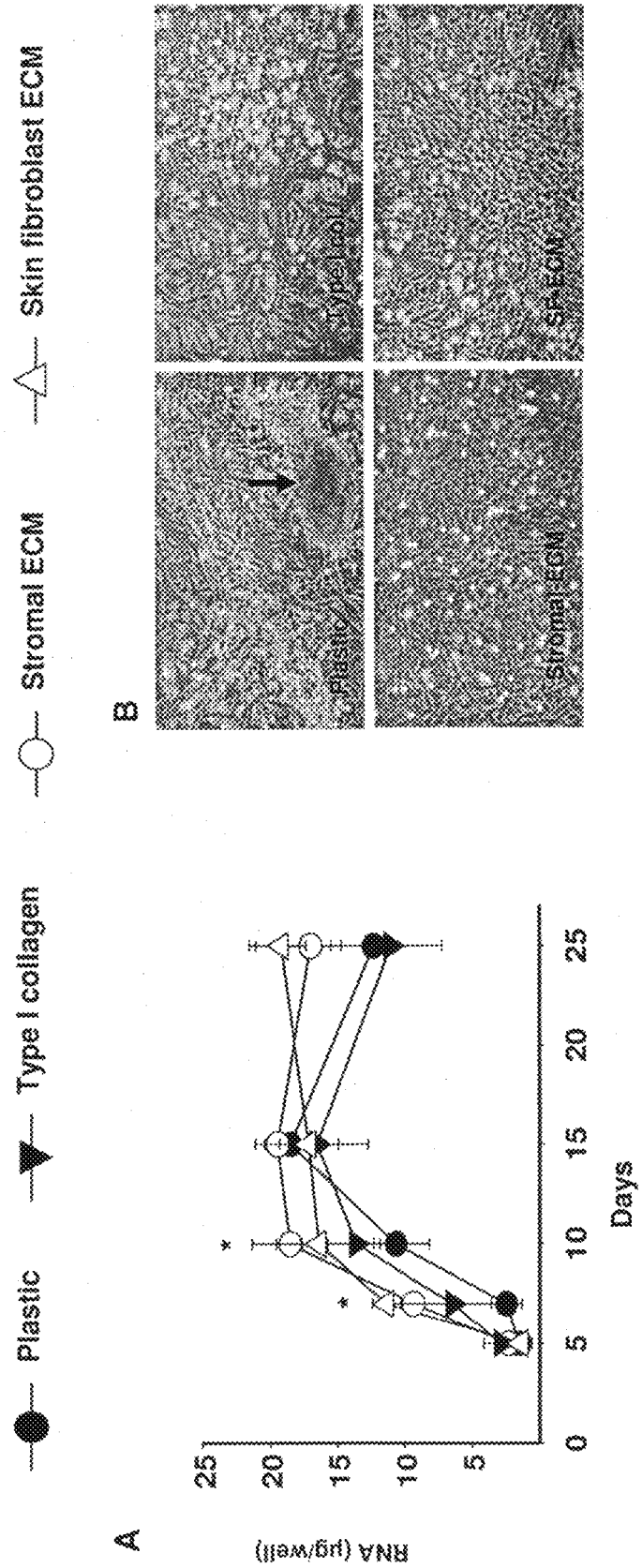
FIG. 4A illustrates behavior of bone marrow cells cultured on 2D and 3D matrices. Primary murine bone marrow cells were placed at $3\times10^5$ cells/cm$^2$ in 6-well plates and cultured on plastic, plastic coated with Type I collagen, marrow stromal cell-derived ECM, or skin fibroblast-derived ECM for 25 days. RNA was extracted from the cell cultures at the indicated time points. Total RNA was obtained at indicated days of culture. * $P<0.05$, n=3 vs. the plastic at the same time point.
FIG. 4B illustrates differentiation of bone marrow cells cultured on 2D and 3D matrices. The appearance of cells cultured on the various culture systems was observed by phase contrast microscopy after 20 days of culture. Original magnification: 200×. The arrow indicates nodules of cells.

The present investors further demonstrate that the marrow stromal cell-derived ECM prevented "spontaneous" differentiation of MSCs. The 2D Type I collagen ECM, and a 3D skin fibroblast-derived ECM (SF-ECM) elaborated by skin fibroblasts obtained from neonatal mice were used as controls. The latter ECM exhibited a fibrillar structure similar to that of marrow stromal cell-derived ECM (data not shown), consistent with the presence of type I and type III collagens. The proliferation of marrow cells placed on these matrices was similar, as determined by RNA content, and was increased as compared to cells cultured on plastic (FIG. 4A). When cultured on plastic for 20 days, cells were grouped into nodules whereas cells cultured on the collagen-containing ECM preparations were evenly distributed and exhibited a uniform morphology (FIG. 4B). The expression of the osteoblast markers alkaline phosphatase, col1a1, bone sialoprotein, and osteocalcin progressively increased during 25 days of culture (FIG. 4C), consistent with the "spontaneous" differentiation of MSCs reported previously. In contrast, stromal cell-derived or skin fibroblast-derived ECM preparations prevented or delayed the appearance of these osteoblast markers. The 2D Type I collagen ECM also retarded osteoblastogenesis, but it was less effective. In a separate experiment, there was minimal mineral deposition, as determined by Von Kossa staining, when cells were maintained on the stromal cell-derived ECM (data not shown).

Figures 4C, 4D:
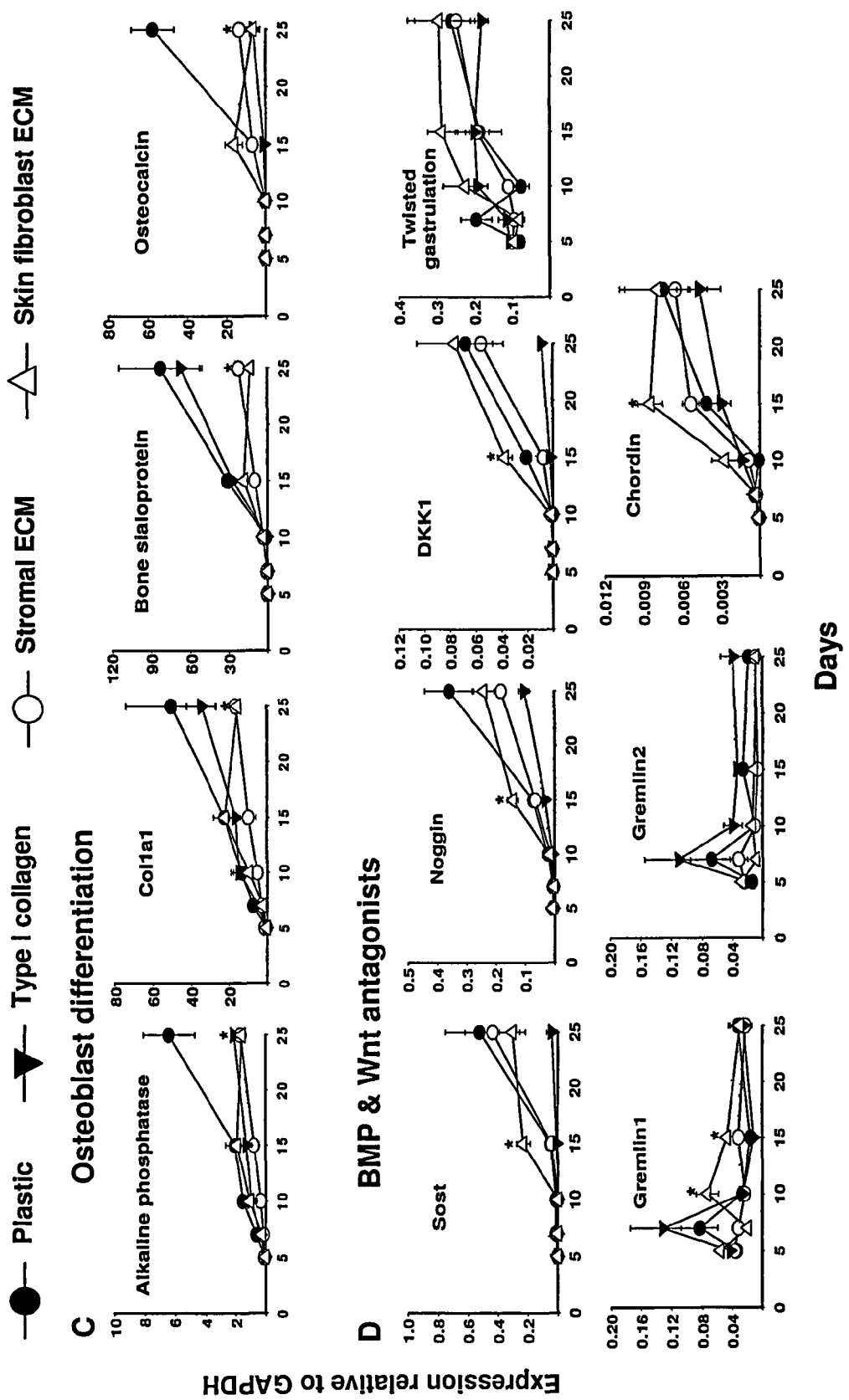
FIG. 4C illustrates the level of transcripts of osteoblastic markers as determined by TaqMan PCR at the indicated days of culture. * $P<0.05$, n=3 vs. the plastic or plastic coated with Type I collagen at the same time point.
FIG. 4D illustrates the level of transcripts for BMP and Wnt antagonists as determined by TaqMan PCR at the indicated days of culture. * $P<0.05$, n=3 vs. plastic, Type I collagen, or the stromal ECM at the same time point.

The restraint of osteoblastogenesis seen in cultures of MSCs maintained on stromal cell-derived ECM did not appear to be due to increased production of antagonists of the bone morphogenetic proteins (BMPs) and Wnt proteins needed for osteoblast differentiation. Specifically, the level of Sost, Noggin, Dkk1, Chordin, Gremlin, and Twisted gastrulation transcripts in cultures maintained on this ECM were equivalent to, or less than, that of cells cultured on plastic (FIG. 4D). A similar pattern was seen in the case of cells cultured on Type I collagen. On the other hand, transcripts of most of these antagonists were higher in cells cultured on the skin fibroblast-derived ECM, except for Gremlin 2 (FIG. 4D).

The marrow stromal cell-derived ECM supported MSC function, whereas the ECM made by skin fibroblasts failed to support responsiveness to exogenous BMP2. The transcript levels of BMP and Wnt antagonists were increased in these cultures.

Example 5

Autocrine/paracrine production of BMP2 mediates the osteoblastogenesis that occurs when MSCs are entered on plastic in the presence of high ascorbic acid.[9] Hence, the restraint of osteoblast differentiation observed in cultures maintained on the stromal cell-derived ECM could have been due to decreased synthesis of endogenous BMP2. The level of BMB2 transcripts, however, was similar to or higher in cultures maintained on the stromal cell-derived or skin fibroblast-derived ECM as compared to cells maintained on plastic (FIG. 5A), making this possibility unlikely. Murine bone marrow cell cultures were established on plastic or on the stromal cell-derived ECM in 6-well plates. After 15 days, the supernatant was collected. BMP2 was extracted from the ECM/cell layer using 2M urea, 2% SDS, 10% glycerol and 10 mM Tris-HCl pH 6.8. BMP2 in the supernatant and in the ECM/cell layer extract was quantified by ELISA.

The cells maintained on the 2D type I collagen ECM expressed low levels of BMP2 compared to the other cultures. A separate experiment demonstrated that the amount of BMP2 protein was increased approximately 2-fold in cultures maintained for 15 days on the stromal cell-derived ECM as compared to plastic (FIG. 5B), and that >90% of BMP2 protein was associated with the cell/matrix in cultures maintained on the stromal cell-derived ECM as compared to only 60% in the case of cultures maintained on the plastic. Thus, the restraint of osteoblast differentiation when MSCs were cultured on this ECM is related to sequestration of BMP2 by the ECM. Moreover, the expression of BMP2R1B transcripts was increased when cells were cultured on collagenous ECM as compared to plastic, indicating that lack of BMP2 receptor does not account for the poor responsiveness of cultures maintained on Type I collagen or skin fibroblast-derived ECM (data not shown).

Figures 5A, 5B, 5C:
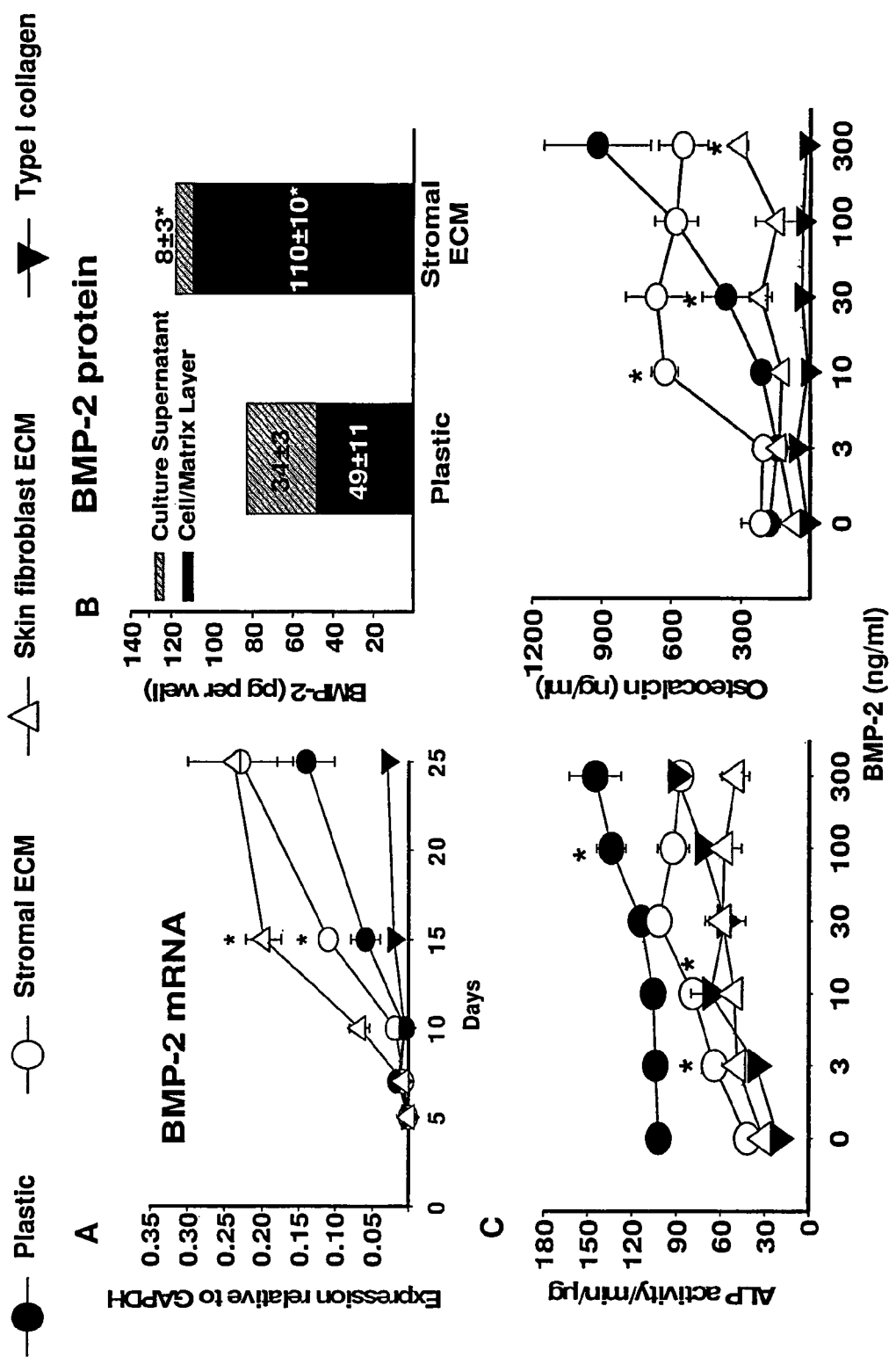
FIG. 5A illustrates production of BMP2 in cultures maintained on 2D and 3D matrices. Level of BMP2 transcripts in the experiment was determined as described in FIG. 3A, * $P<0.05$, n=vs. plastic, Type I collagen at the same time point.
FIG. 5B illustrates production of BMP2 protein in cell/matrix layer or culture supernatant as measured by ELISA assay. * $P<0.05$, n=3 vs. the plastic.
FIG. 5C illustrates responsiveness to exogenous BMP2 by measuring alkaline phosphatase activity (left panel) and osteocalcin (right panel). * $P<0.05$ (n=3) vs. vehicle control.

Although MSCs did not undergo "spontaneous" osteoblastogenesis when cultured on the stromal cell-derived ECM, they were capable of differentiating into osteoblasts in response to exogenous BMP2. When added 15 days after establishment of the cultures, as little as 3 ng/ml or as little as 10 ng/ml of BMP2 stimulated alkaline phosphatase activity and osteocalcin secretion (FIG. 5C). Consistent with the data of FIG. 4C, which shows an increase in alkaline phosphatase transcripts, basal alkaline phosphatase activity was elevated in cultures maintained on tissue culture plastic as compared to the ECM. Addition of exogenous BMP2 to cells maintained on plastic modestly increased alkaline phosphatase activity, as well as osteocalcin secretion, but these effects required 10-fold higher concentrations than the cells cultured on the ECM. BMP2 increased alkaline phosphatase activity, but not osteocalcin secretion, in MSCs maintained on the 2D Type I collagen ECM. MSCs failed to respond to exogenous BMP2 when cultured on skin fibroblast-derived ECM.

Murine bone marrow cell cultures were established either on plastic or plastic coated with a collagenous matrix including marrow stromal cell-derived ECM, skin fibroblast-derived ECM or Type I collagen. After 15 days of culture, human recombinant BMP2 was added at the indicated concentrations. Alkaline phosphatase activity was determined after two days. Osteocalcin from conditioned medium was measured by RIA after six days.

Example 6

Culture of MSCs on Stromal Cell-Derived ECM Promotes Self-Renewal and Retention of Multipotentiality.

Figures 6A, 6B, 6C:
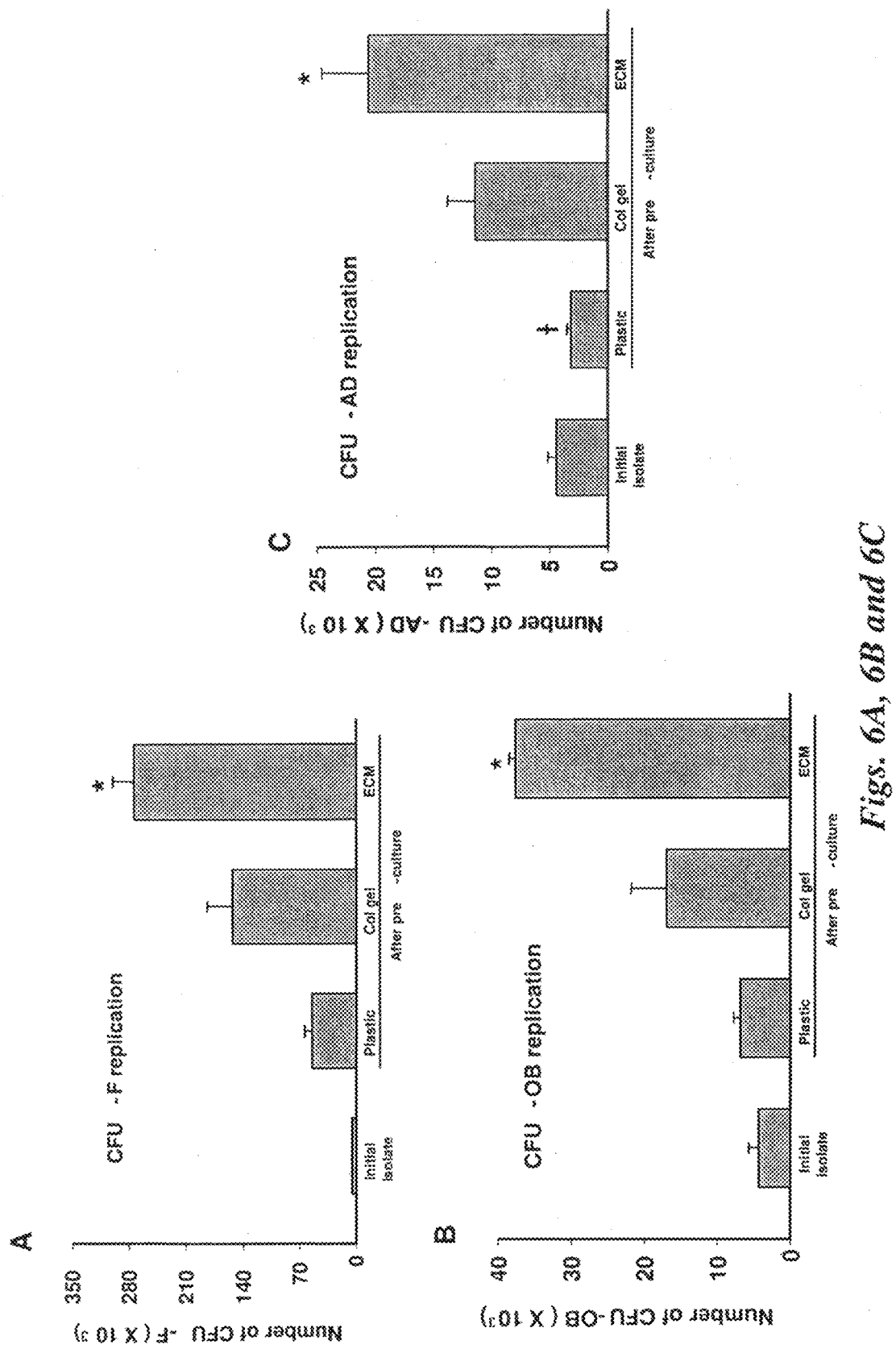
FIG. 6A illustrates CFU-F increased by 9-fold, 27-fold, or 48-fold when cultured on plastic, Type I collagen, or the stromal cell-derived ECM, respectively.
FIG. 6B illustrates CFU-OB increased by 1.6-fold, 4-fold, or 9-fold when cultured on plastic, Type I collagen, or the stromal cell-derived ECM, respectively.
FIG. 6C illustrates CFU-AD changed by 0.7-fold, 2.6-fold, or 4.7-fold when cultured on plastic, Type I collagen, or the stromal cell-derived ECM, respectively. * $P<0.05$ by ANOVA vs. the plastic and Type I collagen gel, n=3. † $P<0.05$, n=3 compared to initial isolated.

The self-renewal of MSCs was determined using a re-plating assay in which the increase in colony forming cells following seven days of pre-culture of MSCs was quantified.[17] Self-renewal of MSCs was measured for MSCs cultured on plastic, the 3D stromal cell-derived ECM, or 3D Type I collagen gels that have been previously described.[9] ECM from skin fibroblasts was not examined as BMP2 responsiveness of MSCs was lost in such cultures. The number of CFU-F colonies was increased approximately 48-fold when the cells were pre-cultured on stromal cell-derived ECM as compared approximately 9-fold or approximately 27-fold in cultures maintained on plastic or Type I collagen gel, respectively (FIG. 6A). Self-renewal of MSCs. Murine bone marrow cells were cultured on plastic, or 3D Type I collagen gel, or the stromal cell-derived ECM at $5 \times 10^6$ cells per 10 cm$^2$ well. Some of the bone marrow cells were used to determine the number of CFU-F, CFU-OB, and CFU-AD present in the initial isolate. After seven days of pre-culture, the adherent-cells were detached and harvested with collagenase, and reseeded into tissue culture plastic for measuring CFU-F, CFU-OB and CFU-AD.

Similarly, the replication of colony-forming progenitors capable of differentiating into osteoblasts [CFU-osteoblast (CFU-OB)] and/or adipocytes [CFU-adipocyte (CFU-AD)], was significantly higher when MSCs were pre-cultured on the stromal cell-derived ECM, as compared to cells cultured on plastic or Type I collagen gel. Indeed, CFU-OB did not significantly increase when pre-cultured on plastic, consistent with the evidence of FIG. 4C that MSCs divided and differentiated toward the osteoblast lineage, instead of dividing to produce identical colony-forming MSCs.

The proportion of CFU-OB and CFU-AD among the entire population of colony-forming MSCs (as detected by CFU-F) declined approximately 3-fold during expansion, from approximately 50% in the initial marrow cell isolate to approximately 15% after pre-culture on plastic, Type I collagen gel, or stromal cell-derived ECM (FIGS. 6B and 6C). This may reflect the heterogeneity of the colony forming cells present in the initial isolate, and the fact that some of the progenitors in the CFU-F population divided more frequently than others during the pre-culture period.

Example 7

Figures 7A, 7B, 7C, 7D:
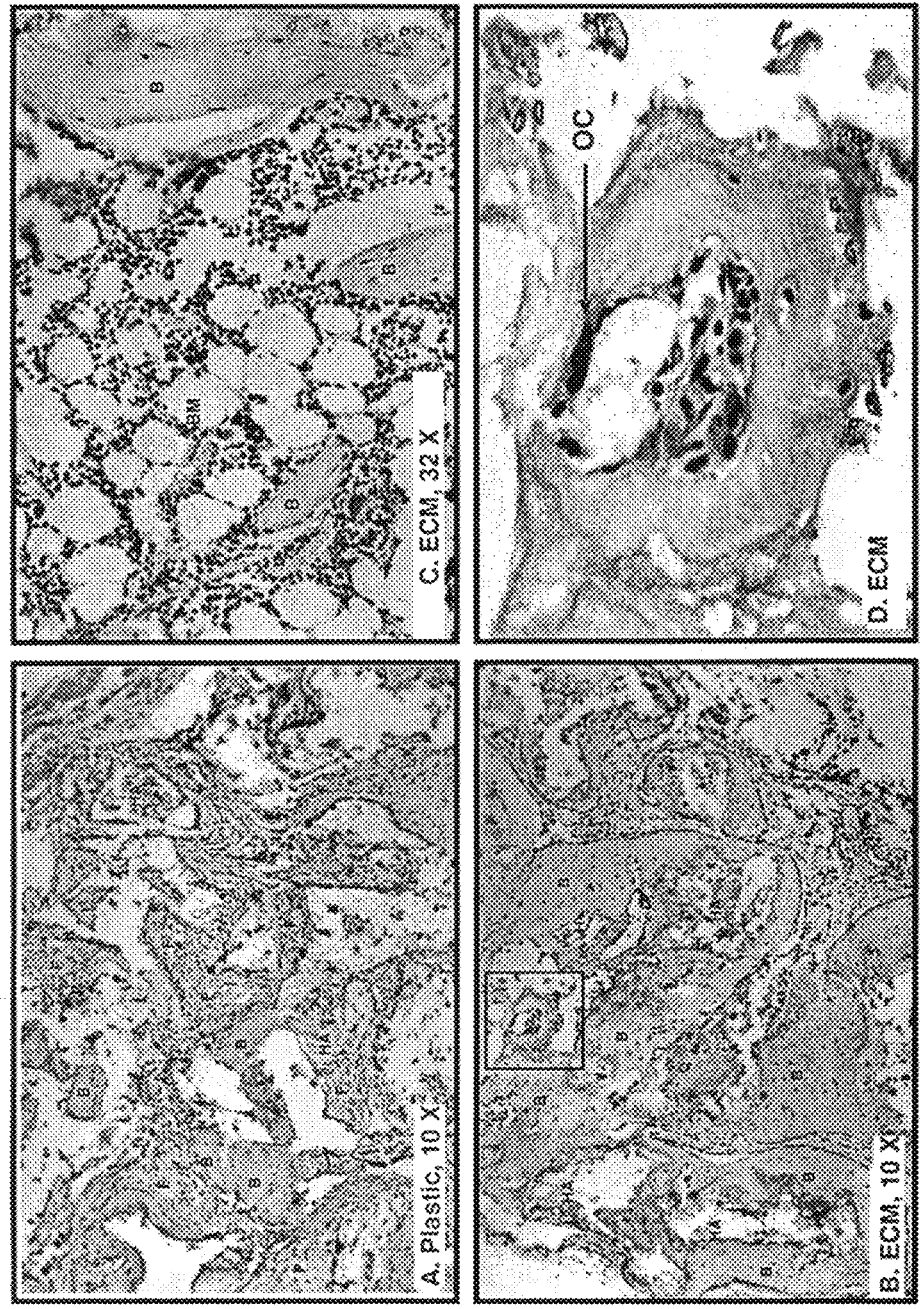
FIG. 7A illustrates bone formation in vivo by transplanted marine MSCs. Bone was generated by cells pre-cultured on plastic.
FIG. 7B illustrates bone generated by cells pre-cultured on the cell-free marrow stromal cell-derived ECM.
FIG. 7C illustrates marrow like structure containing hematopoietic elements in bone generated by cells pre-cultured on the marrow stromal cell derived ECM.
FIG. 7D illustrate an area from FIG. 7B enlarged to demonstrate an osteoclast with multiple nuclei. For FIGS. 7A through 7D, the following legend applies: B, bone; BM, bone marrow with adipocytes and hematopoietic cells; F, fibrous tissue; HA, HA/TCP; OC, osteoclast.
Figures 7E, 7F:
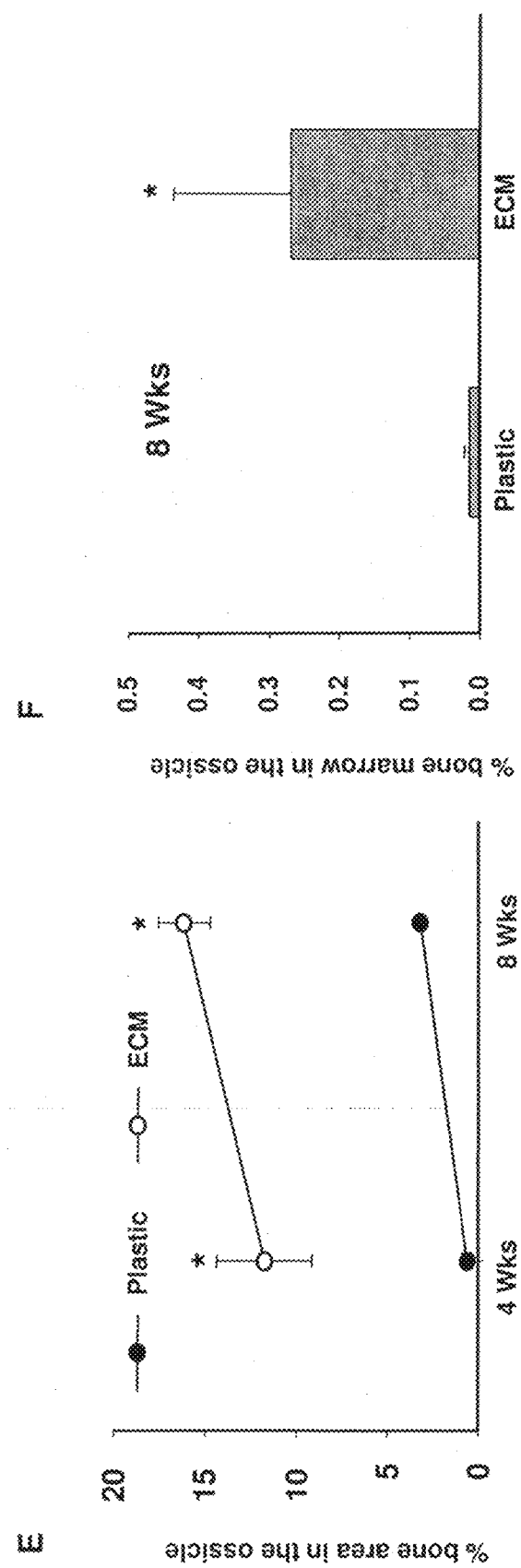
FIG. 7E illustrates the measurement of bone in ossicles. Data shown represent the mean (±sd) of bone area calculated from the 3 individual ossicles.
FIG. 7F illustrates the area occupied by hematopoietic marrow as determined in sections from ossicles obtained 8 weeks alter implantation using the same sections that were used for determination of bone area in FIG. 7E. * $P<0.05$ vs. bone marrow generated by cells pre-cultured on the plastic, n=3.

In view of the likely heterogeneity of the colony forming cell population, the inventors compared the capacity of MSCs expanded on plastic or the stromal cell-derived ECM to form bone and hematopoietic marrow in vivo using a transplantation assay.[19] Following seven days of culture on plastic or on stromal cell-derived ECM, the cells were loaded onto a hydroxyapatite/tricalcium phosphate (HA/TCP) carrier and implanted subcutaneously into immunocompromised NIH-bg-nu-xid mice. The amount of bone generated at eight weeks after implantation by MSCs pre-cultured on plastic was approximately 3% of bone of the total area of the ossicle. However, there was minimal hematopoietic marrow, and adipocytes and osteoclasts were rarely observed (FIGS. 7A, 7B and 7E). Importantly, MSCs pre-cultured on stromal cell-derived ECM generated approximately five times more bone than the cells pre-cultured on tissue culture plastic (FIGS. 7B through 7E), which corresponds with the approximately 5-fold greater increase in CFU-OB replication during pre-culture on the ECM as compared to plastic (FIG. 6B).

Bone marrow cells were pre-cultured for seven days on plastic or the stromal cell-derived ECM. The cells were then loaded onto HA/TCP and implanted subcutaneously into the dorsal surface of 10-week-old immunodeficient beige NIH-bg-nu-xid mice. Three transplants were made for each group. The transplants were harvested after four or eight weeks, fixed, decalcified and then processed for paraffin embedding.

Osteoclasts were also present in ossicles made by cells pre-cultured on the ECM (FIG. 7D), indicating the presence of stromal cells that support osteoclast differentiation. Extensive hematopoietic marrow characterized by a large number of adipocytes was observed at 8, but not 4, weeks after implantation (FIG. 7C). The area of hematopoietic marrow was increased by 8-fold in ossicles made by cells cultured on the ECM as compared to cells cultured on plastic (FIG. 7F). Each ossicle was bisected. Then, 10 μm sections were cut from the bisection point of one portion at 100 μm intervals for measurement of the mean bone area for each ossicle.

Example 8

Primary human bone marrow mononuclear cells (hBMCs, purchased from AllCells, LLC.) were placed onto either the BCM made by human marrow stromal cells (hMSC-ECM) or tissue culture plastic at various cell seeding densities (2, 1, and $0.5 \times 10^6$ cells per well). After 4 hours of incubation, the non-adherent cells were removed by rinsing with PBS once. Then the cells were cultured in α-MEM containing 15% FCS for 2 weeks.

Figure 8:
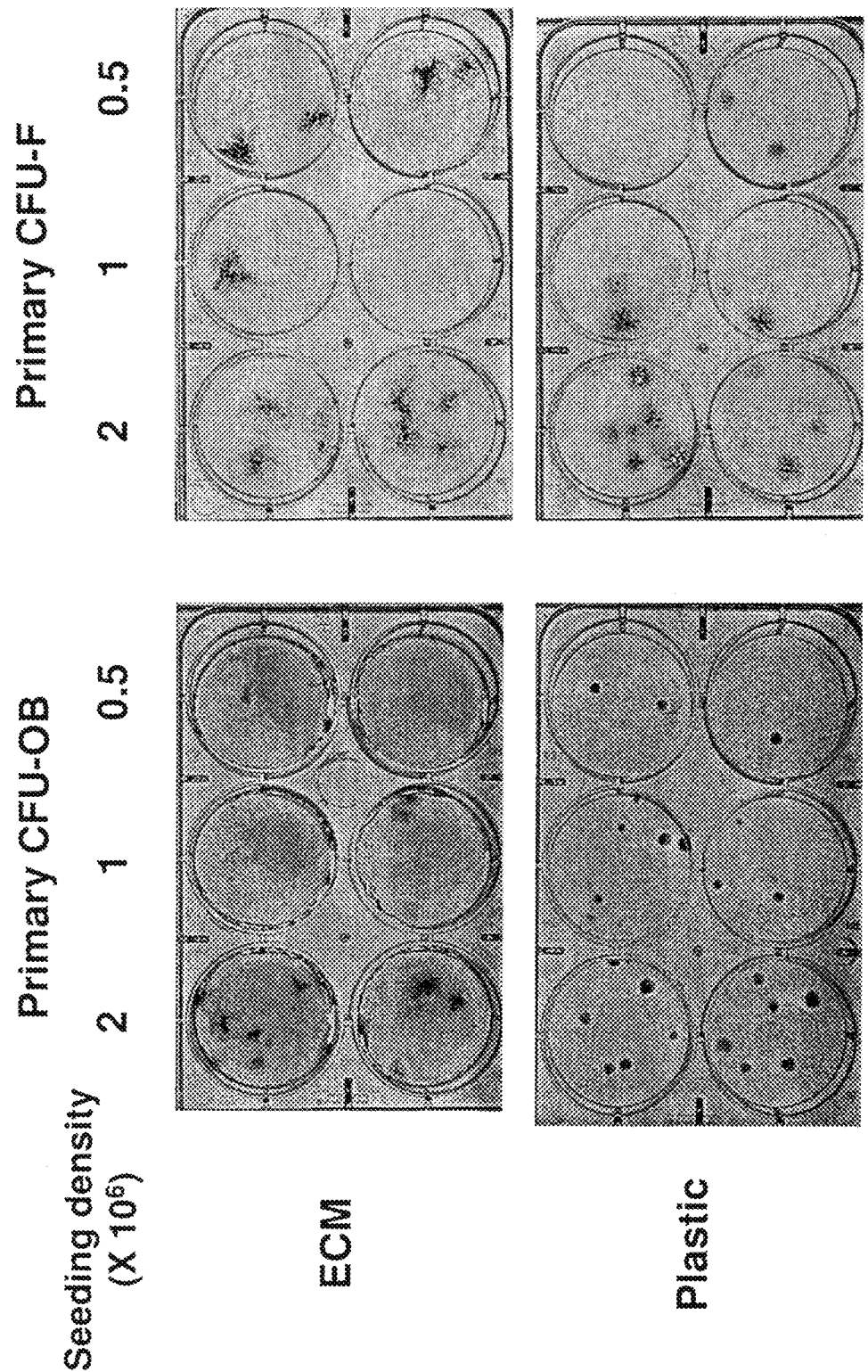
FIG. 8 illustrates ECM made by human marrow stromal cells promotes colony forming unit-osteoblast (CFU-OB) and colony forming unit-fibroblast (CFU-F) formation. CFU-F were visualized by crystal violet shown in blue (right panel). In addition, cells were cultured in osteogenic induction medium ($\alpha$-MEM containing 15% FCS, 100 µM A2P, 10 mM $\beta$-glycerophosphate, and 10 nM dexamethasone) for 4 weeks, and then CFU-OB was determined by Von Kossa staining shown in black (left panel).

FIG. 8 illustrates ECM made by human marrow stromal cells promotes colony forming unit-osteoblast (CFU-OB) and colony forming unit-fibroblast (CFU-F) formation. CFU-F were visualized by crystal violet shown in blue (right panel). In addition, cells were cultured in osteogenic induction medium (α-MEM containing 15% FCS, 100 μM, A2P, 10 mM β-glycerophosphate, and 10 mM dexamethasone) for 4 weeks, and then CFU-OB was determined by Von Kossa staining shown in black (left panel).

Example 9

Figure 9:
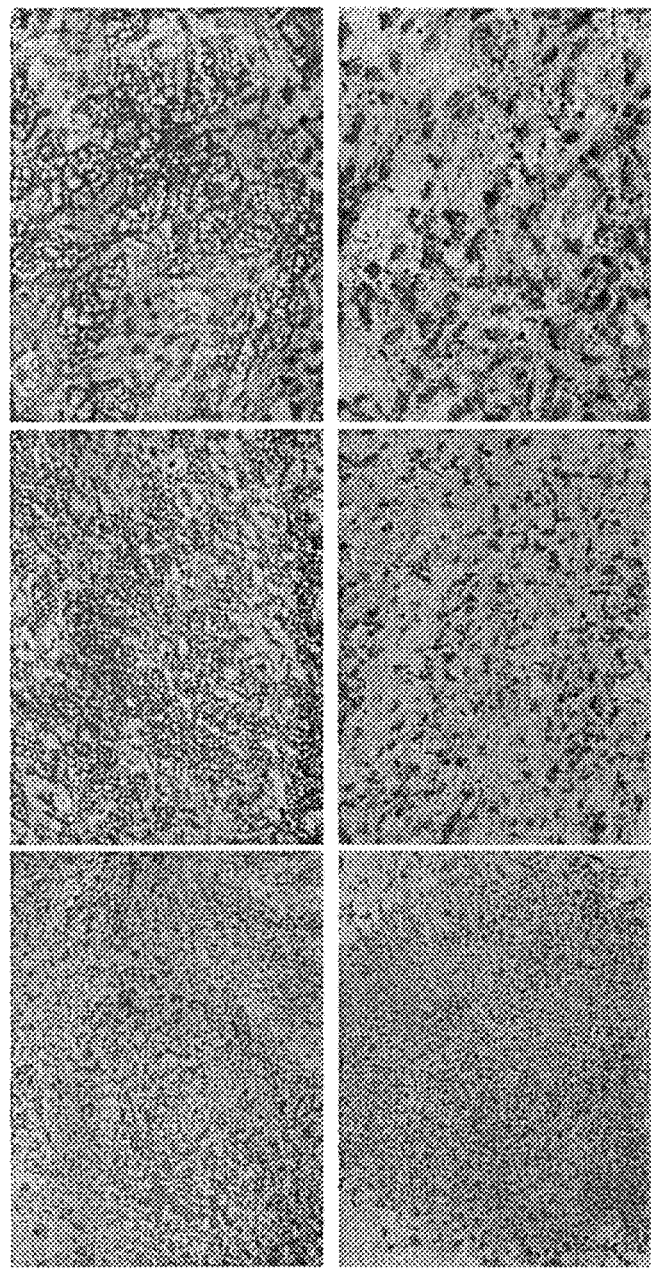
FIG. 9 illustrates microscopic appearance of CFU-OB.

The colonies formed by cells cultured on the BCM contained both osteoblasts as visualized by the deposition of mineral stained with Von Kossa (black), and adipocytes stained with Oil Red O (red). The colonies formed by cells cultured on tissue plastic contained less mineral content and fewer adipocytes. FIG. 9 illustrates microscopic appearance of CFU-OB.

Example 10

Primary human bone marrow mononuclear cells (All-Cells, LLC.) were pre-cultured for 14 days on tissue culture plastic or the human stromal cell-derived ECM. The cells were then loaded onto a transplantation vehicle [hydroxyapatite/tricalcium phosphate (HA/TCP) particles] and implanted subcutaneously into the dorsal surface of 10 weeks old immunodeficient beige NIH-bg-nu-xid mice. The transplants were harvested after 8 weeks, fixed, decalcified and then processed for paraffin embedding.

Figure 10:
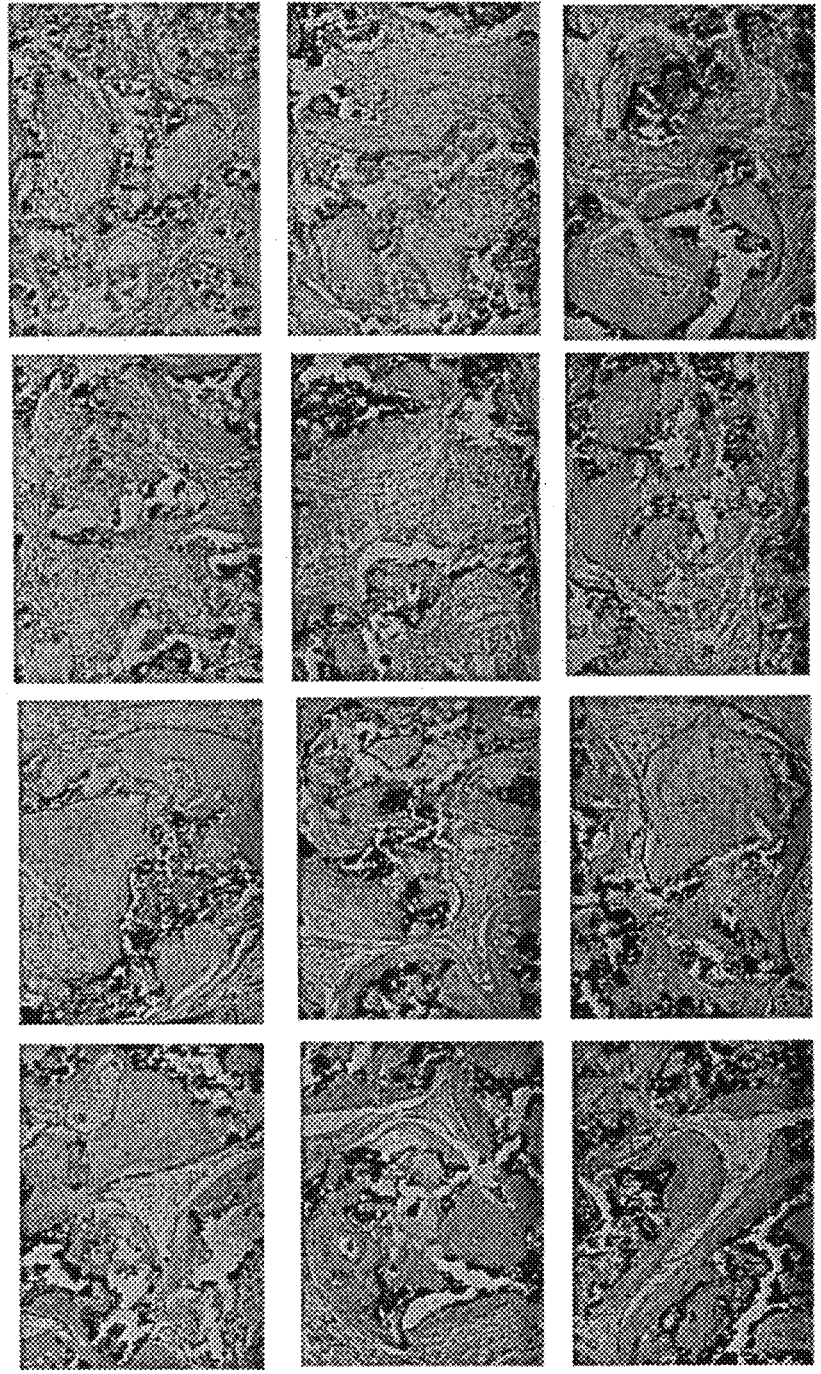
FIG. 10 illustrates bone formation in vivo by transplanted human MSCs. Bone was generated by cells pre-cultured on the ECM (left panel). Bone was generated by cells pre-cultured on tissue culture plastic (right panel).

FIG. 10 illustrates bone formation in vivo by transplanted human MSCs. Bone was generated by cells pre-cultured on the ECM (left panel). Bone was generated by cells pre-cultured on tissue culture plastic (right panel).

Example 11

Figure 11A:
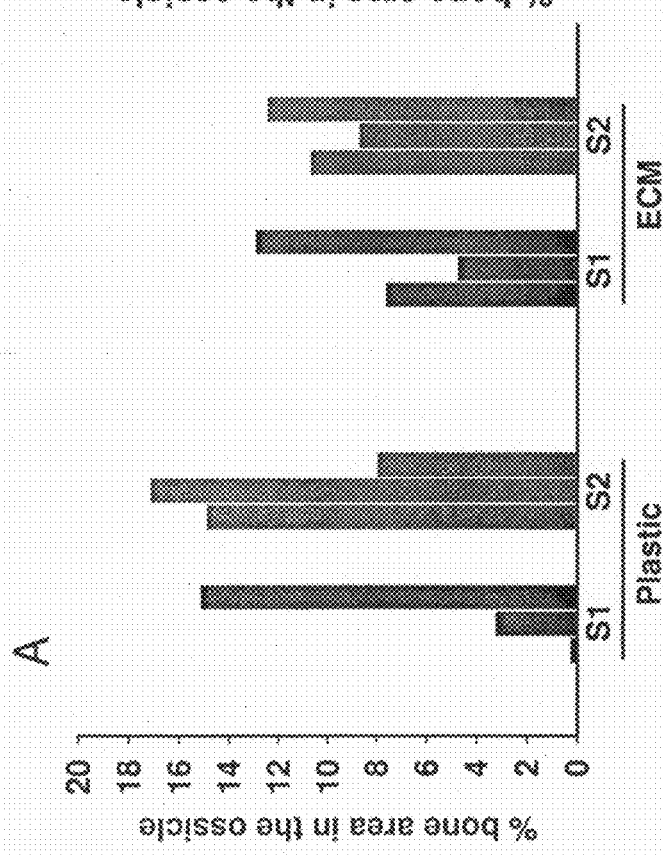
FIGS. 11A and B illustrate quantification of bone in ossicles. Each ossicle was bisected. Then, three 10 µm sections were cut from the center part at 100 µm intervals.
Figure 11B:
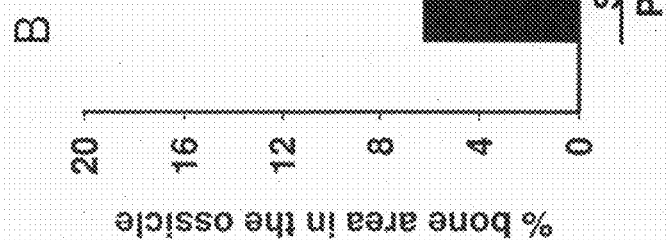
FIG. 11B shows the mean bone area calculated from 3 individual sections for each sample (S1 or S2).

FIGS. 11A and B illustrate quantification of bone in ossicles. Each ossicle was bisected. Then, three 10 μm sections were cut from the center past at 100 μm intervals. FIG. 11A shows the measurements of bone area from 3 individual sections for each sample (S1 or S2). FIG. 11B shows the mean bone area calculated from 3 individual sections for each sample (S1 or S2).

Figure 11C:
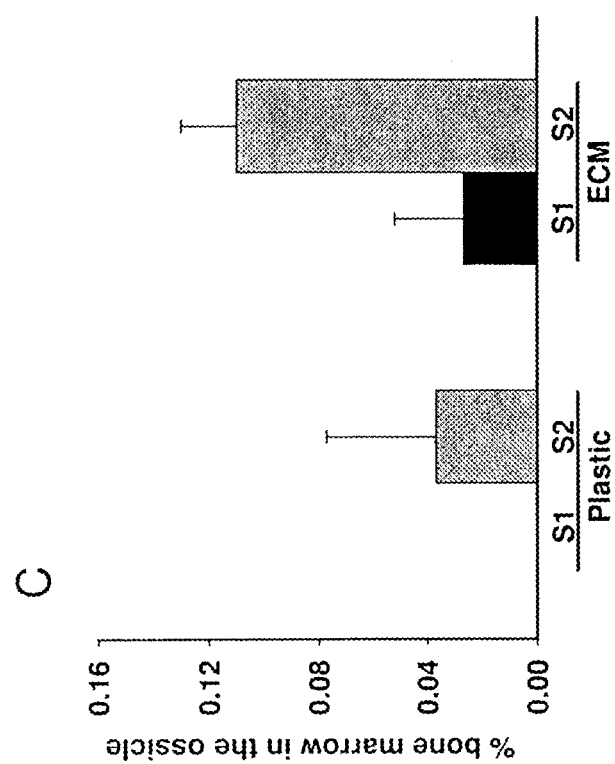
FIG. 11C illustrates quantification of bone marrow in ossicles with mean bone marrow (hematopoietic tissue), calculated from 3 individual sections for each sample.

FIG. 11C illustrates quantification of bone marrow in ossicles with mean bone marrow (hematopoietic tissue) calculated from 3 individual sections for each sample.

REFERENCES

1. Dennis J E, Merriam A, Awadallah A, Yoo J U, Johnstone B, Caplan A I 1999 A quadripotential mesenchymal progenitor cell isolated from the marrow of an adult mouse. J Bone Miner Res 14:700.
2. Moriscot C, de Fraipont F, Richard M J, Marchand M, Savatier P, Bosco D, Favrot M, Benhamou P Y 2005 Human bone marrow mesenchymal stem cells can express insulin and key transcription factors of the endocrine pancreas developmental pathway upon generic and/or microenvironmental manipulation is vitro. Stem Cells 23:594.

3. Engler A J, Sen S, Sweeney H L, Discher D E 2006 Matrix elasticity directs stem cell lineage specification. Cell 126: 677.
4. Blanco P, Riminucci M, Gronthos S, Robey P G 2001 Bone marrow stromal stem cells: nature, biology, and potential applications. Stem Cells 19:180.
5. Katayama Y, Battista M, Kao W M, Hidalgo A, Peired A J, Thomas S A. Frenette P S 2006 Signals from the sympathetic nervous system regulate hematopoietic stem cell egress from bone marrow. Cell 124:407.
6. Klein G 1995 The extracellular matrix of the hematopoietic microenvironment. Experientia 51:914.
7. Bianco F, Fisher L W, Young M F, Termine J D, Robey P G 1990 Expression and localization of the two small proteoglycans biglycan and decorin in developing human skeletal and non-skeletal tissues. J Histochem Cytochem 38:1549.
8. Krebsbach P H, Kuznetsov S A, Satomura K, Emmons R V B, Rowe D W, Robey P G 1997 Bone formation in vivo: comparison of osteogenesis by transplanted mouse and human marrow stromal fibroblasts. Transplantation 63:1059.
9. Abe E, Yamamoto M, Taguchi Y, Lecka-Czernik B, O'Brien C A, Economides A N, Stahl N, Jilka R L, Manolagas S C 2000. Essential requirement of bmps-2/4 for both osteoblast and osteoclast formation in murine bone marrow cultures from adult mice: antagonism by noggin. J Bone Miner Res 15:663.
10. Chen X D, Fisher L W, Robey P G, Young M F 2004 The small leucine-rich proteoglycan biglycan modulates bmp-4-induced osteoblast differentiation. FASEB J 18:948.
11. D'Ippolito G, Diabira S, Howard G A, Menei B, Roos B A, Schiller P C 2004 Marrow-isolated adult multilineage inducible (miami) cells, a unique population of postnatal young and old human cells with extensive expansion and differentiation potential. J Cell Sci 117:2971.
12. D'Ippolito G, Diabira S, Howard G A, Roos B A, Schiller P C 2006 Low oxygen tension inhibits osteogenic differentiation and enhances stemness of human miami cells. Bone 39:513.
13. Chow D C, Wenning L A, Miller W M, Pappoutsakis E T 2001 Modeling pO(2) distributions in the bone marrow hematopoietic compartment. I. Krogh's model. Biophys J 181:675.
14. Jiang Y, Jahagirdar B N, Reinhardt R L, Schwartz R E, Keene C D, Ortiz-Gonzalez X R, Reyes M, Lenvik T, Lund T, Blackstad M, Du J, Aldrich S, Lisberg A, Low W C, Largaespada D A, Verfarllie C M 2002 Pluripotency of mesenchymal stem cells derived from adult marrow. Nature 418:41.
15. Sekiya I, Larson B L, Smith J R, Pochampally R, Cui J G, Prockop D J 2002 Expansion of human adult stem cells from bone marrow stroma: conditions that maximize the yields of early progenitors and evaluate their quality. Stem Cells 20:530.
16. Peister A, Mellad J A, Larson B L, Ball B M, Gibson L F, Prockop D J 2004 Adult stem cells from bone marrow (MSCs) isolated from different strains of inbred mice vary in surface epitopes, rates of proliferation, and differentiation potential. Blood 103:1662.
17. Di Gregorio G B, Yamamoto M, Ali A A, Abe E, Roberson P, Manolagas S C, Jilka R L 2001 Attenuation of the self-renewal of transit-amplifying osteoblast progenitors in the murine bone marrow by 17 beta-estradiol. J Clin Invest 107:803.
18. Mizutani H, Urist M R 1982 The nature of bone morphogenetic protein (bmp) fractions derived from bovine bone matrix gelatin. Clin Orthop Relat Res 213.
19. Bi Y, Stuelten C H, Kilts T, Wadhwa S, Iozzo R V, Robey P G, Chen X D, Young M F 2005 Extracellular matrix proteoglycans control the fate of bone marrow stromal cells, J Biol Chem 280:30481.
20. Gospodarowicz, D, Lepine J, Massoglia S, Wood I 1984 Comparison of the ability of basement membranes produced by corneal endothelial and mouse-derived endodermal PF-HR-9 cells to support the proliferation and differentiation of bovine kidney tubule epithelial cells in vitro. J Cell Biol 99:947.
21. Sethe S, Scott A, Stolzing A 2006 Aging of mesenchymal stem cells. Ageing Res Rev 5:93
22. Baksh D, Song L, Tuan R S 2004 Adult mesenchymal stem cells: characterization, differentiation, and application in cell and gene therapy. J Cell Mol Med 8:301.

All references cited in this specification are hereby incorporated by reference in their entirety. The discussion of the references herein Is intended merely to summarize the assertions made by their authors and no admission is made that any reference constitutes prior art relevant to patentability. Applicant reserves the right to challenge the accuracy and pertinence of the cited references.

As various changes could be made in the above methods and compositions without departing from the scope of the invention, it is intended that all matter contained in the above description be interpreted as illustrative and not in a limiting sense. Unless explicitly stated to recite activities that have been done (i.e., using the past tense), illustrations and examples are not intended to be a representation that given embodiments of this invention have, or have not, been performed.

What is claimed is:

1. A method of maintaining mammalian mesenchymal stem cells in culture in an undifferentiated state comprising culturing mammalian mesenchymal stem cells in the presence of an extracellular matrix, wherein said extracellular matrix comprises type I collagen, type III collagen, type V collagen, syndecan-1, fibronectin, decorin, biglycan, perlecan, and laminin.

2. The method of claim 1 wherein said mammalian mesenchymal stem cells are selected from the group consisting of human mesenchymal stem cells and murine mesenchymal stem cells.

3. The method of claim 1 wherein said extracellular matrix is a marrow stromal cell derived extracellular matrix.

4. The method of claim 1 wherein said extracellular matrix is a three-dimensional matrix.

* * * * *